US009675615B2

(12) United States Patent
Gillet et al.

(10) Patent No.: US 9,675,615 B2
(45) Date of Patent: Jun. 13, 2017

(54) 2,3-DIHYDROQUINAZOLIN-4(1H)-ONE DERIVATIVES FOR USE IN THE TREATMENT OF VIRAL INFECTIONS

(71) Applicants: COMMISSARIAT A L'ENERGIE ATOMIQUE ET AUX ENERGIES ALTERNATIVES, Paris (FR); UNIVERSITY OF TEXAS MEDICAL BRANCH, Galveston, TX (US)

(72) Inventors: Daniel Gillet, Antony (FR); Julien Barbier, Gif-Sur-Yvette (FR); Robert Davey, Helotes, TX (US); Jean-Christophe Cintrat, Igny (FR); Romain Noel, Trevou-Treguinec (FR)

(73) Assignees: Commissariat a l'Energie Atomique et aux Energies Alternatives, Paris (FR); The Board of Regents of the University of Texas System, Austin, TX (US)

( * ) Notice: Subject to any disclaimer, the term of this patent is extended or adjusted under 35 U.S.C. 154(b) by 0 days.

(21) Appl. No.: 14/436,390

(22) PCT Filed: Oct. 18, 2013

(86) PCT No.: PCT/EP2013/071867
§ 371 (c)(1),
(2) Date: Apr. 16, 2015

(87) PCT Pub. No.: WO2014/060588
PCT Pub. Date: Apr. 24, 2014

(65) Prior Publication Data
US 2015/0250788 A1    Sep. 10, 2015

(30) Foreign Application Priority Data

Oct. 19, 2012  (EP) .................................... 12306299

(51) Int. Cl.
| | | |
|---|---|---|
| *A01N 43/00* | (2006.01) | |
| *A61K 31/517* | (2006.01) | |
| *C07D 409/04* | (2006.01) | |
| *C07D 409/14* | (2006.01) | |
| *C07D 239/91* | (2006.01) | |
| *C07D 417/14* | (2006.01) | |

(52) U.S. Cl.
CPC .......... *A61K 31/517* (2013.01); *C07D 239/91* (2013.01); *C07D 409/04* (2013.01); *C07D 409/14* (2013.01); *C07D 417/14* (2013.01)

(58) Field of Classification Search
CPC .................................................... A61K 31/517
USPC .................................................... 514/266.21
See application file for complete search history.

(56) References Cited

U.S. PATENT DOCUMENTS

| | | | | |
|---|---|---|---|---|
| 3,316,269 A | * | 4/1967 | Schipper .............. | C07D 401/04 544/284 |
| 9,540,356 B2 | * | 1/2017 | Gillet .................... | C07D 409/04 |
| 2009/0163545 A1 | * | 6/2009 | Goldfarb .............. | A61K 31/122 514/312 |
| 2011/0201601 A1 | | 8/2011 | Gillet et al. | |
| 2015/0166517 A1 | * | 6/2015 | Atwood ............... | C07D 403/04 514/266.24 |

FOREIGN PATENT DOCUMENTS

| | | | | | |
|---|---|---|---|---|---|
| EP | WO 2009153457 | | * | 12/2009 | ........... A61K 31/506 |
| WO | 2009153457 A2 | | | 12/2009 | |
| WO | 2010103306 A1 | | | 9/2010 | |
| WO | 2011046646 A2 | | | 4/2011 | |
| WO | WO 2014014814 | | * | 1/2014 | ........... A61K 31/506 |

OTHER PUBLICATIONS

Venkatesh et al., J. Pharm. Sci. 89, 145-54 (2000) (p. 146, left column).*
Park et al. Nature Scientific Reports. 2012. 2; 63.*
Noel et al. Journal of Medicinal Chemistry, 2013, 56, 3413-34-13.*
International Search Report issued in corresponding International Patent Application No. PCT/EP2013/071867 dated Jan. 16, 2014.
Written Opinion issued in corresponding International Patent Application No. PCT/EP2013/071867 dated Jan. 16, 2014.
Jewn Giew Park et al. "Chemical Structure of Retro-2, a Compound That Protects Cells against Ribosome-Inactivating Proteins", Scientific Reports, vol. 2, pp. 1-4, (2012).
Romain Noel et al. "N-Methyldihydroquinozolinone Derivatives of Retro-2 with Enhanced Efficacy against Shiga Toxin", Journal of Medicinal Chemistry, vol. 56, pp. 3404-3413, (2013).
Neetu Gupta et al. "(S)-N-Methyldihydroquinazolinones are the Active Enantiomers of Retro-2 Derived Compounds against Toxins", ACS Medicinal Chemistry Letters, (2013).

* cited by examiner

*Primary Examiner* — Nizal Chandrakumar
(74) *Attorney, Agent, or Firm* — Morgan, Lewis & Bockius LLP

(57) ABSTRACT

Use of 2,3-dihydroquinazolin-4(1H)-one cyclic derivatives of formula (I) for the treatment of infection with viruses entering cells by endocytosis, especially filovirus such as Ebolavirus.

(I)

13 Claims, 1 Drawing Sheet

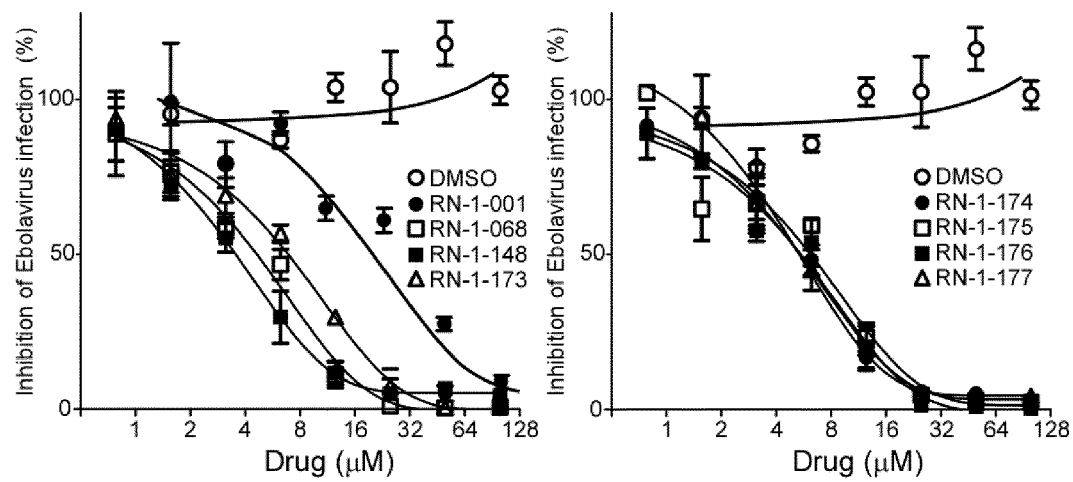

2,3-DIHYDROQUINAZOLIN-4(1H)-ONE DERIVATIVES FOR USE IN THE TREATMENT OF VIRAL INFECTIONS

The present invention relates to the use of 2,3-dihydroquinazolin-4 (1H)-one cyclic derivatives for the treatment of infection with viruses entering cells by endocytosis, especially filovirus such as Ebolavirus.

Ebolavirus (EBOV) is a filovirus member of the Filoviridae family. Five Ebolavirus species are identified on nucleotide sequence and serology: Bundibugyo, Reston, Sudan, Tai Forest and Zaire.

All filoviruses are filamentous, enveloped and of polymorphic size, with filaments ranging in length from 0.3 to several microns. They are emerging viruses with sporadic outbreaks reported at 2-10 year intervals since the initial identification of outbreak fatal hemorrhagic fever in 1976 near the Ebola River, Democratic Republic of the Congo, Africa. Ebola virus is one of the most widely publicized viruses infectious to people. All species except Reston cause severe disease with the Zaire species associated with 80 to 90% mortality (Peters, C. J. 1996. West J Med 164:36-8).

Aside from palliative treatment, there is no effective vaccine or drug for prevention or treatment of filovirus infection. The broad-spectrum antiviral, ribavirin, is ineffective against filoviruses (Huggins, J. W. 1989. Rev Infect Dis 11 Suppl 4:S750-61) and has significant side-effects that include generalized cell toxicity, anemia and mood changes.

Transfusion of convalescent patient serum has been shown to be useful; however careful dosing is required to avoid neurological complications (Mupapa et al. 1999. J Infect Dis 179 Suppl 1:S18-23).

Some success has been found using monoclonal antibodies against Ebolavirus glycoproteins and nucleoproteins (Xu et al. 1998. Nat Med 4:37-42) and candidate vaccines are being tested (Pushko et al. 2001. J Virol 75:11677-85) but are not approved or available to the public. These vaccines also show limited efficacy when administered after infection has taken place. However, reducing virus titers in the blood has been shown to be effective in preventing death in non-human primate models (Sullivan et al. 2006. PLoS Med 3:e177) indicating that therapeutic interventions that give a 10-100-fold reduction in virus titer may aid in recovery. However, new therapies remain needed as those currently available have significant drawbacks.

Previous research has suggested that mononuclear phagocytic cells and endothelial cells are sites of early Ebolavirus replication although evidence of replication has been observed in many tissues including the liver, spleen and lymph nodes (Connolly et al. 1999. J Infect Dis 179 Suppl 1:S203-17; Geisbert et al. 2000. Lab Invest 80:171-86; Nabel, G. J. 1999. Nat Med 5:373-4; Schnittler et al. 1993. J Clin Invest 91:1301; Yang et al. 1998. Science 279:1034-7). The broad range of cells that can be infected suggests a role for monocytes in dispersing the virus to distant sites of the body (Schnittler, H. J., and H. Feldmann. 1998. Clin Infect Dis 27:404-6 and 1999. Curr Top Microbiol Immunol 235:175-204; Stroher et al. 2001. J Virol 75:11025-33). In animal models, infected monocytes can be found early in infection and at distal sites from the site of inoculation. It has been proposed that cytokines released from infected mononuclear cells contribute to the hypotensive shock, vascular permeability and cell damage seen during the later course of infection that is believed to lead to death. Apoptosis is also seen in endothelial cells from fatally infected patients (Baize et al. 1999. Nat Med 5:423-6).

The entry of viruses is the first step for establishing an infection. Entry comprises the distinct steps of binding single or multiple receptors on cells, internalization or uptake and trafficking through endosomes and finally membrane fusion of the virus membrane with the endosomal membrane. Disruption of any one of these steps results in loss of virus infectivity and prevention of spread to neighboring cells. The virus glycoproteins (GPs) that extend from the virion surface play important key roles in each entry step. However, host cell proteins that are targeted by virus proteins are also important for establishing infection. Other proteins that drive cellular processes used by the virus for infection are also potential targets for intervention. Disrupting the function of such proteins has a direct impact on the virus. Temporary disruption of cell processes is well tolerated by the cell. However, such disruption can be lethal to the virus as virus becomes redirected to sites within the cell that are non-productive for infection. Inventors have demonstrated that this is true for Ebolavirus; disruption of PI3 kinase signaling, which is needed for early steps in entry, by the drug LY294002, results in sequestration of virus to early endosomes and loss of infectivity (Saeed et al. 2008. PLoS Pathogens 4:e1000141). Removal of the drug does not restore infection and so indicates virus has been redirected into a dead-end destructive endocytic compartment. Drugs that disrupt steps in virus entry are used in the clinic to treat virus infections by other viruses: Maraviroc blocks HIV glycoprotein interaction with its cell receptor (Wasmuth, et al. 2012. Expert Opin Drug Saf 11:161-74); Stachyflin and Enfuvirtide disrupt membrane fusion of the virus with cell and endosomal membranes (Hsieh, H. P., and J. T. Hsu. 2007. Curr Pharm Des 13:3531-42).

The entry pathway of Ebolavirus has been explored in high detail. The virus requires uptake into the cell through the endosomal pathway. The inventors' published work has shown that Ebolavirus enters cells by macropinocytosis (Hunt et al. 2010, J Virol; Saeed et al. 2010. PLoS Pathog 6). This is a specialized pathway where the cell engulfs large particles in the extracellular medium. The virus is then taken into acidified endosomes in which the viral glycoprotein is cleaved by cysteine proteases to form an active viral glycoprotein (Chandran et al. 2005. Science 308:1643-5). Further acidification results in a structural rearrangement of the glycoprotein and membrane fusion of the virus envelope with the endosomal membrane. Recently, others reported that the Neimann Pick protein (NPC1) is a critical factor in promoting infection. Chemicals that disrupt the function of NPC1 also disrupt infection by Ebolavirus. The exact mechanism remains unclear but this protein represents a distinct target to that proposed in the present submission (Carette et al. 2011. Nature 477:340-3; Cote et al. 2011. Nature 477:344-8). Drugs that block cysteine protease activity or NPC1 function are effective in blocking Ebolavirus infection in culture. However, neither has been shown effective in any animal model.

In later work, Inventors have observed that Ebolavirus requires trafficking to Golgi-associated compartments in the cell to infect cells (Saeed et al. 2008. PLoS Pathogens 4:e1000141). Ebolavirus particles have been observed associated with Golgi related proteins are in proximity to the Golgi in cells. In addition, disruption of the Golgi by treatment of cells with Brefeldin A or NDGA resulted in loss of infectivity by Ebolavirus. This evidence supports the conclusion that Ebolavirus requires uptake and trafficking to compartments that are closely associated with or are in the Golgi complex. To become associated with the Golgi, virus must have entered the retrograde endocytic pathway. Therefore drugs that target and inhibit the retrograde endocytic pathway could be effective in preventing infection of the cell.

While Marburg virus is not as well studied as Ebolavirus, it shows similar patterns of infection and dependencies on the same cellular proteins and pathways that are necessary for Ebolavirus infection. Even though the Ebolavirus and Marburg virus glycoproteins (a representative virus gene) share 30% amino acid identity, several data have demonstrated similar dependencies on cysteine proteases, endocytic function and PI3kinase of the two viruses.

As described above, current treatments involve the use of convalescent patient serum, which has significant associated risk from allergic type responses to treatment as well as contraction of other blood-borne diseases. Serum supply is also limited given that most people die from infection. This lack of treatment options demonstrates a need for new therapeutics for filovirus induced disease.

Small molecules able to protect cells and/or animals against Ebola virus by various means have previously been described (Yermolina et al. J Med Chem. 2011; Basu et al. J Virol. 2011, 85:3106-19; Opsenica et al. 2011 J Med Chem. 10; 54:1157-69; Warren et al. 2010 Antimicrob Agents Chemother. 54:2152-9).

In recent years, the search for new molecules to block the intracellular routing of pathogens has accelerated. The main advantage of such molecules relies on their large spectrum activity, since these molecules can effectively protect the cells against various pathogens that share the same intracellular pathways to infect host cell. For some of them targeting the retrograde route, their intracellular target has been identified. However, these molecules, such as Brefeldin A (Donta S. T. et al., *J. Infect. Dis.* 1995 171, 721-4.), Exo-2 (Spooner R. A. et al. *Biochem J.* 2008, 414, 471-84; Yarrow J. C. et al. *C.C.H.T.S.* 2003, 6, 279-86.), Golgicide (Saenz J. B. et al. *Nat. Chem. Biol.* 2009, 5, 157-65) and others (Saenz J. B. et al. *Infect. Imm.* 2007, 75, 4552-61) are cytotoxic because they target some key functions of cellular homeostasis and cannot be used for therapeutic purposes. For other molecules identified by high throughput screening as inhibitors of the action of ricin and/or Shiga toxins, the cellular target is unknown; among them, Retro-1 and Retro-2 have been identified (Stechmann B. et al. *Cell* 2010, 141, 231-42.).

Other research strategies have also been chosen such as siRNA-based therapies, antibodies, or development of others small molecules inhibitors (not targeting the retrograde route): US 2007/0203073; US 2009/0186849, US 2011/0152344, WO 2011/11447, WO 2011/46646, WO 2011/71574, WO 2008/156853 and WO 2011/130419.

Ebolavirus is readily transmitted and rapidly fatal, and there is no effective vaccine or drug therapy. This lack of treatment options demonstrates a need for new therapeutics for filovirus induced disease.

The objective of the invention is thus the identification of molecules having anti-Ebolavirus activity, capable of protecting cells and potentially, animal and human organisms, against Ebolavirus infection and more generally against viruses entering cells by endocytosis, such as filovirus.

Inventors have for the first time demonstrated that a selection of 2,3-dihydroquinazolin-4(1H)-one cyclic derivatives targeting the retrograde pathway show a strong inhibition of the intracellular routing of filovirus and can reduce Ebolavirus infectivity. These molecules are also efficient against any other viruses infecting cells according to mechanisms similar to that of Ebolavirus such as but not limited to Marburg virus.

The biological activity of said selection of 2,3-dihydroquinazolin-4(1H)-one cyclic derivatives according to the present invention has been compared to Retro-2$^{cycl}$ which considered by Inventors to be one of the most efficient inhibitor of the cell retrograde pathway described in the art (EP2145873; WO2009/153457; WO2009/153665; Stechmann B. et al., *Cell* 2010, 141, 231-42; Park et al. Chemical Structure of Retro-2, a Compound That Protects Cells against Ribosome-Inactivating Proteins. *Nature Scientific Reports.* 2012. 2; 631).

The present invention thus concerns the compounds of formula (I):

$$(I)$$

wherein
$R^1$ is a hydrogen atom, a halogen atom or a $C_1$-$C_3$ alkoxy group;
$R^2$ is:
  a phenyl radical optionally substituted by: a phenyl radical, a group —$CF_3$, a halogen atom, a group —$SO_2$-phenyl; a group —S—X or —O—X, X being a $C_1$-$C_4$ alkyl, preferably a methyl; a $C_1$-$C_4$ alkoxy group; a PEG substituent of general formula —($CH_2$—$CH_2$—O)$_n$—R with n=1 à 10, preferably n=1, and R is a hydrogen atom or a methyl group, preferably R is a methyl group; or a group —CO—O—Y or —CO—Y, Y being an hydrogen atom, a $C_1$-$C_4$ alkyl group, a phenyl radical or an allyl group (—$CH_2$—CH=$CH_2$);
  single or fused aromatic heterocyclic groups having 5 to 10 atoms including one or two nitrogen atom(s), preferably a pyridine;
  an adamantyl group, optionally substituted by —OH;
$R^3$ is:
  an aromatic heterocyclic group having 5 or 6 atoms, said heterocyclic group may be selected in the group consisting of thiophene, furan, pyrrole, pyrroline, pyrrolidine, dioxolan, oxazole, thiazole, imidazole, imidazoline, imidazolidine, pyrazole, isoxazole, isothiazole, pyran, pyridine, piperidine, dioxan, morpholine, pyridazine, pyrimidine, pyrazine, preferably, thiophene or pyridine; said aromatic heterocyclic group is optionally substituted by:
    a $C_1$-$C_3$ alkyl group, preferably a methyl;
    a halogen atom;
    a phenyl group optionally substituted by one or more of: $C_1$-$C_3$ alkoxy group, a group —CN, —$NO_2$, —COX or —COOX, X being a $C_1$-$C_4$ alkyl radical, preferably a methyl;
    a group —SY, Y being a $C_1$-$C_4$ alkyl group or a phenyl group;
    —CN;
    a group —$CH_2$—$N_3$;
    an aromatic heterocyclic group having 5 or 6 atoms, said aromatic heterocyclic group may be selected in the group consisting of furan, thiophene, pyrrole, pyrroline, pyrrolidine, dioxolane, oxazole, thiazole, imidazole, imidazoline, imidazolidine, pyrazole, isoxazole, isothiazole, pyran, pyridine, piperidine, dioxan, morpholine, pyridazine, pyrimidine, pyrazine, preferably, said aromatic heterocyclic group is a thiophene, pyridine, furan or thiazole; optionally substituted by at least one $C_1$-$C_3$ alkyl radical and/or a group —$CH_2$—$N_3$;

a phenyl group; optionally substituted by $C_1$-$C_3$ alkoxy group or $NMe_2$;

$R^4$ is a hydrogen atom or a methyl group with the proviso that compound of formula is not such as $R^1$ is a hydrogen atom, $R^2$ is a phenyl group, $R^3$ is a 5-methylthiophen-2-yl group and $R^4$ is a hydrogen atom, or their pharmaceutically acceptable salts, for use in the treatment of infection caused by virus that uses retrograde route of uptake or egress, in particular, the treatment of infection by virus entering cell by endocytosis.

The present invention also relates to method of treatment of infection caused by virus that uses retrograde route of uptake or egress, in particular, the treatment of infection by virus entering cell by endocytosis, comprising the administration of an efficient amount of a compound of general formula (I) as described above to a mammalian in need thereof.

The present invention also relates to pharmaceutically acceptable salt of compounds of formula (I) such as hydrochloride, hydrobromide, sulphate or bisulphate, phosphate or hydrogen, acetate, oxalate, benzoate, succinate, fumarate, maleate, lactate, citrates, tartrate, gluconate, methanesulphonate, benzene-sulphonate and paratoluene-sulphonate.

By halogen atom is meant the chemical elements of group VII of the periodic table of elements; including fluorine, chlorine, bromine and iodine. The preferred halogen is bromine (Br) and fluorine (F).

The term $C_1$-$C_3$ or $C_1$-$C_4$ alkyl group means a linear or branched chain of 1 to 3 or 4 carbon atoms, respectively; said chain may be for example methyl, ethyl, propyl, isopropyl or tertiobutyl.

The term $C_1$-$C_3$ or $C_1$-$C_4$ alkoxy group represents a group —$OC_nH_{2n+1}$, n being an integer comprised between 1 and 3 or 1 and 4, respectively, preferably, n is 1; said group may be for example methoxy, ethoxy, propyloxy or isopropyloxy.

Compounds of formula (I) may be chosen from:

| code | Compound | structure | name |
|---|---|---|---|
| RN-1-013 | 1 | 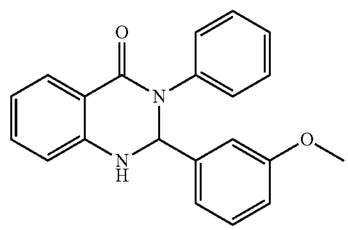 [SMILES: COc1cccc(C2Nc3ccccc3C(=O)N2c2ccccc2)c1] | 2-(3-Methoxyphenyl)-3-phenyl-2,3-dihydroquinazolin-4(1H)-one |
| RN-1-019 | 2 | 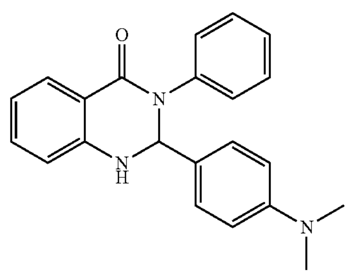 [SMILES: CN(C)c1ccc(C2Nc3ccccc3C(=O)N2c2ccccc2)cc1] | 2-(4-(Dimethylamino)phenyl)-3-phenyl-2,3-dihydroquinazolin-4(1H)-one |
| RN-1-021 | 3 | 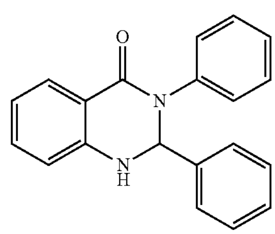 [SMILES: O=C1c2ccccc2NC(c2ccccc2)N1c1ccccc1] | 2,3-Diphenyl-2,3-dihydroquinazolin-4(1H)-one |
| RN-1-027 | 4 | 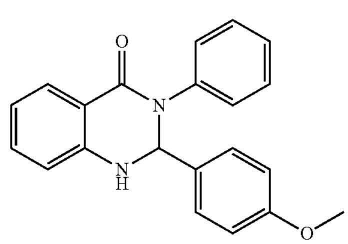 [SMILES: COc1ccc(C2Nc3ccccc3C(=O)N2c2ccccc2)cc1] | 2-(4-Methoxyphenyl)-3-phenyl-2,3-dihydroquinazolin-4(1H)-one |

-continued

| code | Compound | structure | name |
|---|---|---|---|
| RN-1-066 | 5 | 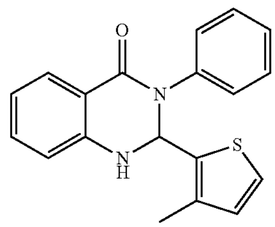 [SMILES: Cc1ccsc1C1Nc2ccccc2C(=O)N1c1ccccc1] | 2-(3-Methylthiophen-2-yl)-3-phenyl-2,3-dihydroquinazolin-4(1H)-one |
| RN-1-067 | 6 | 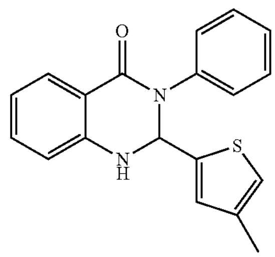 [SMILES: Cc1csc(C2Nc3ccccc3C(=O)N2c2ccccc2)c1] | 2-(4-Methylthiophen-2-yl)-3-phenyl-2,3-dihydroquinazolin-4(1H)-one |
| RN-1-068 | 7 | 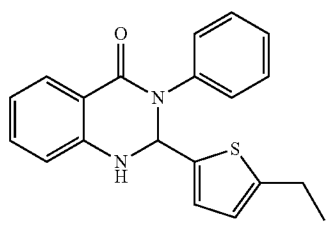 [SMILES: CCc1ccc(C2Nc3ccccc3C(=O)N2c2ccccc2)s1] | 2-(5-Ethylthiophen-2-yl)-3-phenyl-2,3-dihydroquinazolin-4(1H)-one |
| RN-1-086 | 8 | 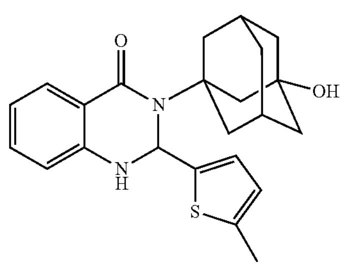 [SMILES: Cc1ccc(C2Nc3ccccc3C(=O)N2C23CC4CC(CC(O)(C4)C2)C3)s1] | 3-((5R,7S)-3-Hydroxyadamantan-1-yl)-2-(5-methylthiophen-2-yl)-2,3-dihydroquinazolin-4(1H)-one |
| RN-1-100 | 9 | 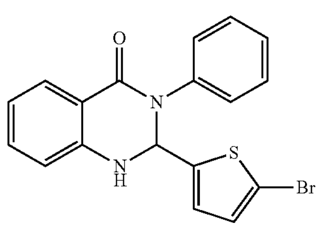 [SMILES: O=C1c2ccccc2NC(c2ccc(Br)s2)N1c1ccccc1] | 2-(5-Bromothiophen-2-yl)-3-phenyl-2,3-dihydroquinazolin-4(1H)-one |
| RN-1-118 | 10 | 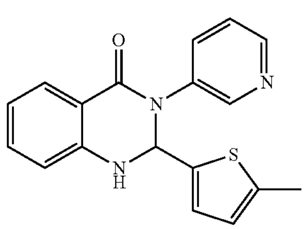 [SMILES: Cc1ccc(C2Nc3ccccc3C(=O)N2c2cccnc2)s1] | 2-(5-Methylthiophen-2-yl)-3-(pyridin-3-yl)-2,3-dihydroquinazolin-4(1H)-one |

-continued

| code | Compound | structure | name |
|---|---|---|---|
| RN-1-120 | 11 | 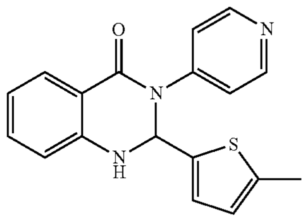 [SMILES: Cc1ccc(C2Nc3ccccc3C(=O)N2c2ccncc2)s1] | 2-(5-Methylthiophen-2-yl)-3-(pyridin-4-yl)-2,3-dihydroquinazolin-4(1H)-one |
| RN-1-132 | 12 | 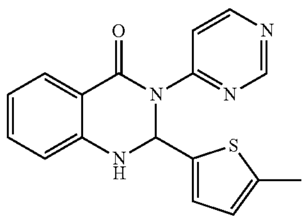 | 2-(5-Methylthiophen-2-yl)-3-(pyrimidin-4-yl)-2,3-dihydroquinazolin-4(1H)-one |
| RN-1-148 | 13 | 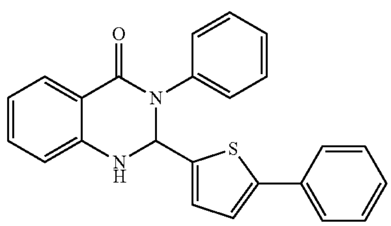 [SMILES: O=C1c2ccccc2NC(c2ccc(-c3ccccc3)s2)N1c1ccccc1] | 3-Phenyl-2-(5-phenylthiophen-2-yl)-2,3-dihydroquinazolin-4(1H)-one |
| RN-1-149 | 14 | 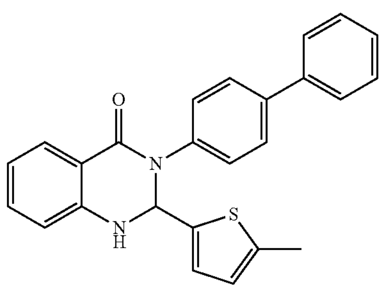 [SMILES: Cc1ccc(C2Nc3ccccc3C(=O)N2c2ccc(-c3ccccc3)cc2)s1] | 3-([1,1'-Biphenyl]-4-yl)-2-(5-methylthiophen-2-yl)-2,3-dihydroquinazolin-4(1H)-one |
| RN-1-151 | 15 | 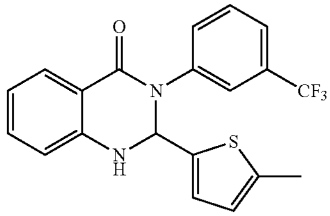 [SMILES: Cc1ccc(C2Nc3ccccc3C(=O)N2c2cccc(C(F)(F)F)c2)s1] | 2-(5-Methylthiophen-2-yl)-3-(3-(trifluoromethyl)phenyl)-2,3-dihydroquinazolin-4(1H)-one |
| RN-1-162 | 16 | 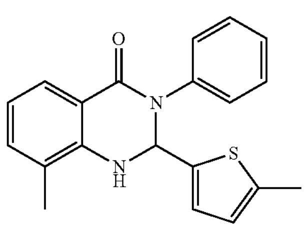 [SMILES: Cc1ccc(C2Nc3c(C)cccc3C(=O)N2c2ccccc2)s1] | 8-Methyl-2-(5-methylthiophen-2-yl)-3-phenyl-2,3-dihydroquinazolin-4(1H)-one |

-continued

| code | Compound | structure | name |
| --- | --- | --- | --- |
| RN-1-173 | 17 | 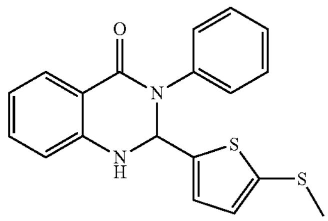 [SMILES: CSc1ccc(C2Nc3ccccc3C(=O)N2c2ccccc2)s1] | 2-(5-(Methylthio)thiophen-2-yl)-3-phenyl-2,3-dihydroquinazolin-4(1H)-one |
| RN-1-174 | 18 | 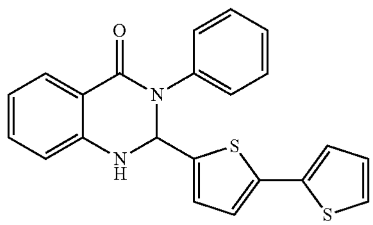 [SMILES: O=C1c2ccccc2NC(c2ccc(-c3cccs3)s2)N1c1ccccc1] | 2-([2,2'-Bithiophen]-5-yl)-3-phenyl-2,3-dihydroquinazolin-4(1H)-one |
| RN-1-175 | 19 | 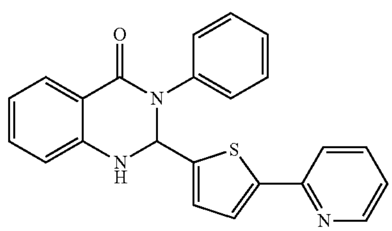 [SMILES: O=C1c2ccccc2NC(c2ccc(-c3ccccn3)s2)N1c1ccccc1] | 3-Phenyl-2-(5-(pyridin-2-yl)thiophen-2-yl)-2,3-dihydroquinazolin-4(1H)-one |
| RN-1-176 | 20 | 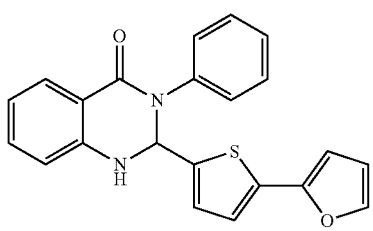 [SMILES: O=C1c2ccccc2NC(c2ccc(-c3ccco3)s2)N1c1ccccc1] | 2-(5-(Furan-2-yl)thiophen-2-yl)-3-phenyl-2,3-dihydroquinazolin-4(1H)-one |
| RN-1-177 | 21 | 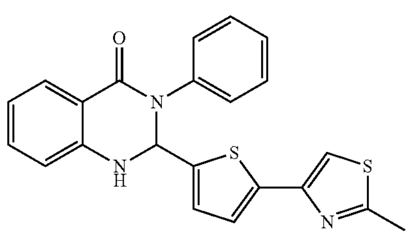 [SMILES: Cc1nc(-c2ccc(C3Nc4ccccc4C(=O)N3c3ccccc3)s2)cs1] | 2-(5-(2-Methylthiazol-4-yl)thiophen-2-yl)-3-phenyl-2,3-dihydroquinazolin-4(1H)-one |
| RN-2-120 | 22 | 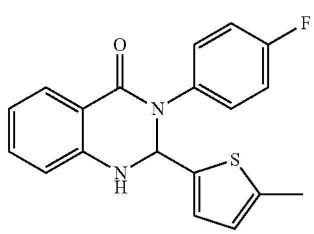 [SMILES: Cc1ccc(C2Nc3ccccc3C(=O)N2c2ccc(F)cc2)s1] | 3-(4-Fluorophenyl)-2-(5-methylthiophen-2-yl)-2,3-dihydroquinazolin-4(1H)-one |

| code | Compound | structure | name |
| --- | --- | --- | --- |
| RN-2-137 | 23 | 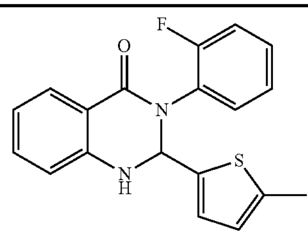 | 3-(2-Fluorophenyl)-2-(5-methylthiophen-2-yl)-2,3-dihydroquinazolin-4(1H)-one |
| RN-2-161 | 24 | 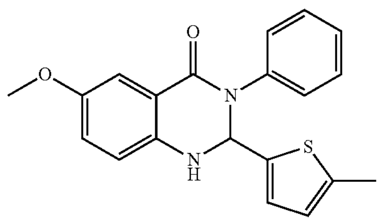 | 6-Methoxy-2-(5-methylthiophen-2-yl)-3-phenyl-2,3-dihydroquinazolin-4(1H)-one |
| RN-2-162 | 25 | 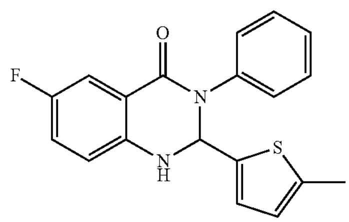 [SMILES: Cc1ccc(C2Nc3ccc(F)cc3C(=O)N2c2ccccc2)s1] | 6-Fluoro-2-(5-methylthiophen-2-yl)-3-phenyl-2,3-dihydroquinazolin-4(1H)-one |
| RN-2-163 | 26 | 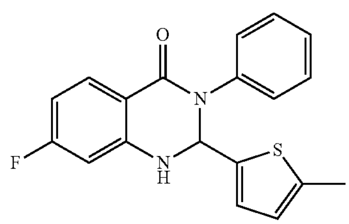 [SMILES: Cc1ccc(C2Nc3cc(F)ccc3C(=O)N2c2ccccc2)s1] | 7-Fluoro-2-(5-methylthiophen-2-yl)-3-phenyl-2,3-dihydroquinazolin-4(1H)-one |
| RN-2-177 | 27 | 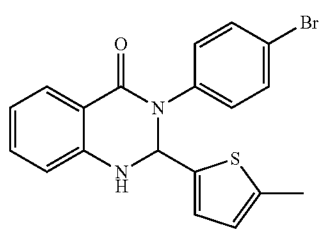 [SMILES: Cc1ccc(C2Nc3ccccc3C(=O)N2c2ccc(Br)cc2)s1] | 3-(4-Bromophenyl)-2-(5-methylthiophen-2-yl)-2,3-dihydroquinazolin-4(1H)-one |
| RN-2-178 | 28 | 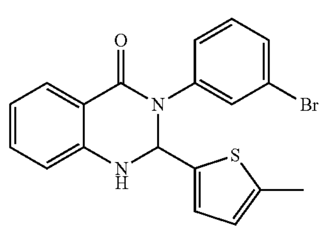 [SMILES: Cc1ccc(C2Nc3ccccc3C(=O)N2c2cccc(Br)c2)s1] | 3-(3-Bromophenyl)-2-(5-methylthiophen-2-yl)-2,3-dihydroquinazolin-4(1H)-one |
| RN-2-180 | 29 | 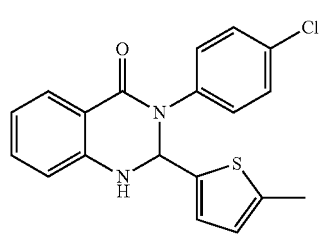 [SMILES: Cc1ccc(C2Nc3ccccc3C(=O)N2c2ccc(Cl)cc2)s1] | 3-(4-Chlorophenyl)-2-(5-methylthiophen-2-yl)-2,3-dihydroquinazolin-4(1H)-one |

-continued

| code | Compound | structure | name |
| --- | --- | --- | --- |
| RN-2-181 | 30 | 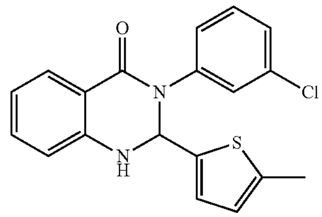 [SMILES: Cc1ccc(C2Nc3ccccc3C(=O)N2c2cccc(Cl)c2)s1] | 3-(3-Chlorophenyl)-2-(5-methylthiophen-2-yl)-2,3-dihydroquinazolin-4(1H)-one |
| RN-2-183 | 31 | 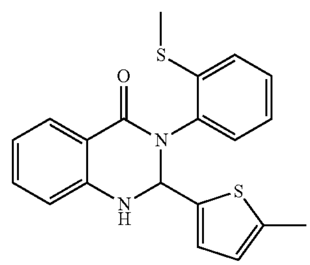 [SMILES: CSc1ccccc1N1C(=O)c2ccccc2NC1c1ccc(C)s1] | 3-(2-(Methylthio)phenyl)-2-(5-methylthiophen-2-yl)-2,3-dihydroquinazolin-4(1H)-one |
| RN-2-182 | 32 | 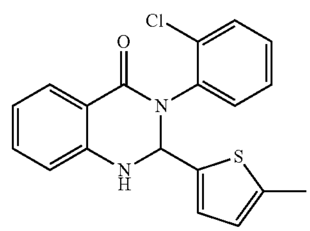 [SMILES: Cc1ccc(C2Nc3ccccc3C(=O)N2c2ccccc2Cl)s1] | 3-(2-Chlorophenyl)-2-(5-methylthiophen-2-yl)-2,3-dihydroquinazolin-4(1H)-one |
| RN-2-199 | 33 | 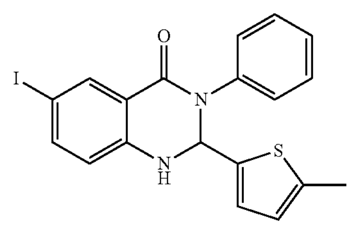 [SMILES: Cc1ccc(C2Nc3ccc(I)cc3C(=O)N2c2ccccc2)s1] | 6-Iodo-2-(5-methylthiophen-2-yl)-3-phenyl-2,3-dihydroquinazolin-4(1H)-one |
| RN-3-121 | 34 | 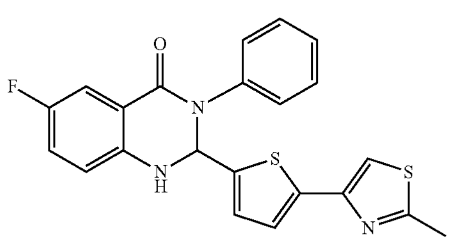 [SMILES: Cc1nc(-c2ccc(C3Nc4ccc(F)cc4C(=O)N3c3ccccc3)s2)cs1] | 6-fluoro-2-(5-(2-methylthiazol-4-ypthiophen-2-yl)-3-phenyl-2,3-dihydroquinazolin-4(1H)-one |
| RN-1-181 | 35 | 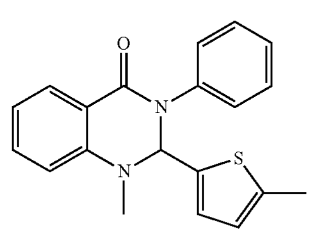 [SMILES: Cc1ccc(C2N(C)c3ccccc3C(=O)N2c2ccccc2)s1] | 1-Methyl-2-(5-methylthiophen-2-yl)-3-phenyl-2,3-dihydroquinazolin-4(1H)-one |

-continued

| code | Compound | structure | name |
|---|---|---|---|
| RN-1-186 | 36 | 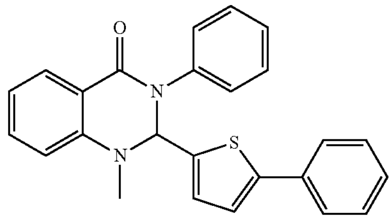 [SMILES: CN1c2ccccc2C(=O)N(c2ccccc2)C1c1ccc(-c2ccccc2)s1] | 1-Methyl-3-phenyl-2-(5-phenylthiophen-2-yl)-2,3-dihydroquinazolin-4(1H)one |
| RN-1-192 | 37 | 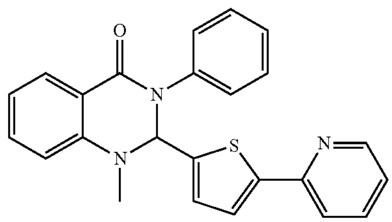 | 1-Methyl-3-phenyl-2-(5-(pyridin-2-yl)thiophen-2-yl)-2,3-dihydroquinazolin-4(1H)-one |
| RN-1-196 | 38 | 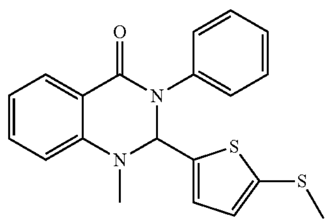 [SMILES: CSc1ccc(C2N(C)c3ccccc3C(=O)N2c2ccccc2)s1] | 1-Methyl-2-(5-(methylthio)thiophen-2-yl)-3-phenyl-2,3-dihydroquinazolin-4(1H)-one |
| RN-1-197 | 39 | 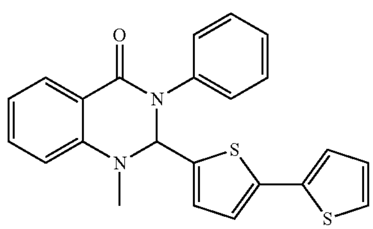 [SMILES: CN1c2ccccc2C(=O)N(c2ccccc2)C1c1ccc(-c2cccs2)s1] | 2-([2,2'-Bithiophen]-5-yl)-1-methyl-3-phenyl-2,3-dihydroquinazolin-4(1H)-one |
| RN-2-001 | 40 | 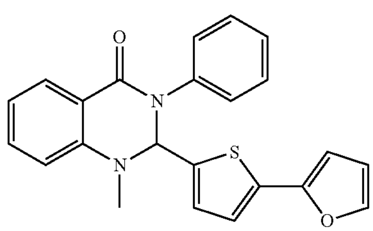 [SMILES: CN1c2ccccc2C(=O)N(c2ccccc2)C1c1ccc(-c2ccco2)s1] | 2-(5-(Furan-2-yl)thiophen-2-yl)-1-methyl-3-phenyl-2,3-dihydroquinazolin-4(1H)-one |
| RN-2-005 | 41 | 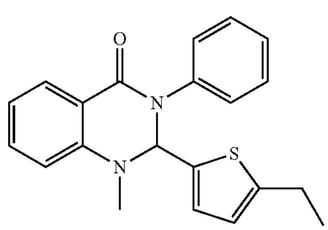 [SMILES: CCc1ccc(C2N(C)c3ccccc3C(=O)N2c2ccccc2)s1] | 2-(5-Ethylthiophen-2-yl)-1-methyl-3-phenyl-2,3-dihydroquinazolin-4(1H)-one |

-continued

| code | Compound | structure | name |
| --- | --- | --- | --- |
| RN-2-015 | 42 | 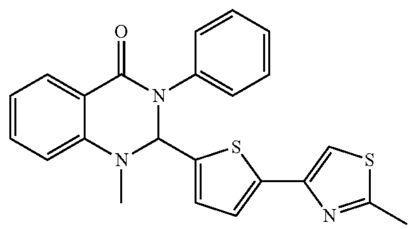 [SMILES: Cc1nc(-c2ccc(C3N(C)c4ccccc4C(=O)N3c3ccccc3)s2)cs1] | 1-Methyl-2-(5-(2-methylthiazol-4-yl)thiophen-2-yl)-3-phenyl-2,3-dihydroquinazolin-4(1H)-one |
| RN-2-016 | 43 | 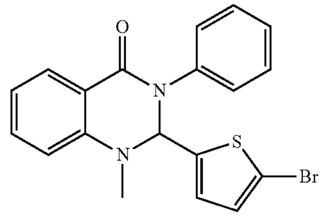 [SMILES: CN1c2ccccc2C(=O)N(c2ccccc2)C1c1ccc(Br)s1] | 2-(5-Bromothiophen-2-yl)-1-methyl-3-phenyl-2,3-dihydroquinazolin-4(1H)-one |
| RN-2-019 | 44 | 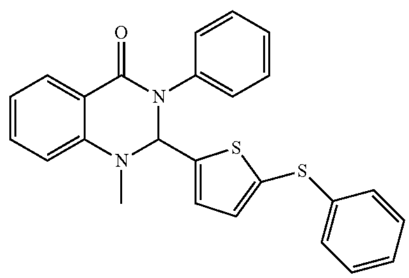 [SMILES: CN1c2ccccc2C(=O)N(c2ccccc2)C1c1ccc(Sc2ccccc2)s1] | 1-Methyl-3-phenyl-2-(5-(phenylthio)thiophen-2-yl)-2,3-dihydroquinazolin-4(1H)-one |
| RN-2-029 | 45 | 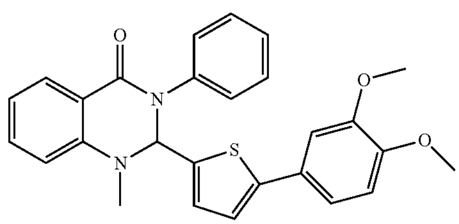 [SMILES: COc1ccc(-c2ccc(C3N(C)c4ccccc4C(=O)N3c3ccccc3)s2)cc1OC] | 2-(5-(3,4-Dimethoxyphenyl)thiophen-2-yl)-1-methyl-3-phenyl-2,3-dihydroquinazolin-4(1H)-one |
| RN-2-032 | 46 | 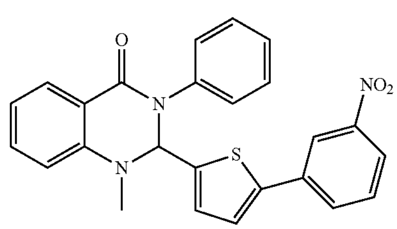 [SMILES: CN1c2ccccc2C(=O)N(c2ccccc2)C1c1ccc(-c2cccc([N+](=O)[O-])c2)s1] | 1-Methyl-2-(5-(3-nitrophenyl)thiophen-2-yl)-3-phenyl-2,3-dihydroquinazolin-4(1H)-one |
| RN-2-034 | 47 | 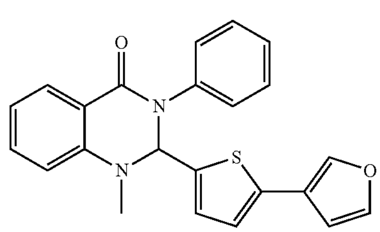 [SMILES: CN1c2ccccc2C(=O)N(c2ccccc2)C1c1ccc(-c2ccoc2)s1] | 2-(5-(Furan-3-yl)thiophen-2-yl)-1-methyl-3-phenyl-2,3-dihydroquinazolin-4(1H)-one |

-continued

| code | Compound | structure | name |
| --- | --- | --- | --- |
| RN-2-049 | 48 | 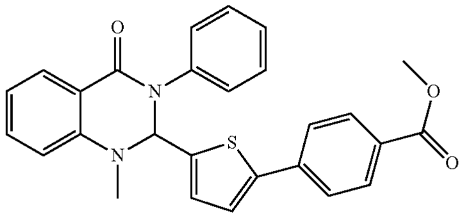 [SMILES: COC(=O)c1ccc(-c2ccc(C3N(C)c4ccccc4C(=O)N3c3ccccc3)s2)cc1] | Methyl 4-(5-(1-methyl-4-oxo-3-phenyl-1,2,3,4-tetrahydroquinazolin-2-yl)thiophen-2-yl)benzoate |
| RN-2-050 | 49 | 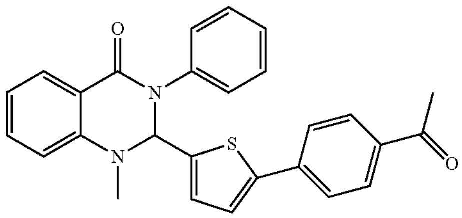 [SMILES: CC(=O)c1ccc(-c2ccc(C3N(C)c4ccccc4C(=O)N3c3ccccc3)s2)cc1] | 2-(5-(4-Acetylphenyl)thiophen-2-yl)-1-methyl-3-phenyl-2,3-dihydroquinazolin-4(1H)-one |
| RN-2-053 | 50 | 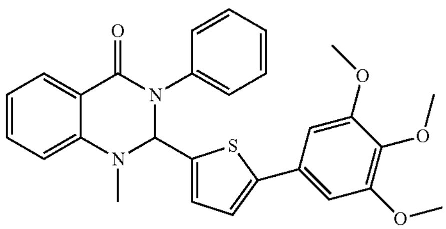 [SMILES: COc1cc(-c2ccc(C3N(C)c4ccccc4C(=O)N3c3ccccc3)s2)cc(OC)c1OC] | 1-Methyl-3-phenyl-2-(5-(3,4,5-trimethoxyphenyl)thiophen-2-yl)-2,3-dihydroquinazolin-4(1H)-one |
| RN-2-057 | 51 | 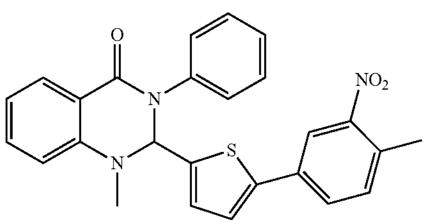 [SMILES: Cc1ccc(-c2ccc(C3N(C)c4ccccc4C(=O)N3c3ccccc3)s2)cc1[N+](=O)[O-]] | 1-methyl-2-(5-(4-methyl-3-nitrophenyl)thiophen-2-yl)-3-phenyl-2,3-dihydroquinazolin-4(1H)-one |
| RN-2-059 | 52 | 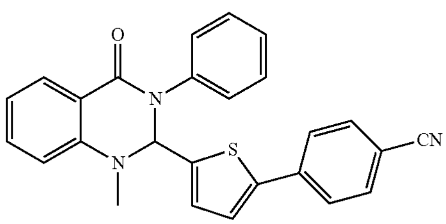 [SMILES: CN1c2ccccc2C(=O)N(c2ccccc2)C1c1ccc(-c2ccc(C#N)cc2)s1] | 4-(5-(1-Methyl-4-oxo-3-phenyl-1,2,3,4-tetrahydroquinazolin-2-yl)thiophen-2-yl)benzonitrile |
| RN-3-012 | 53 | 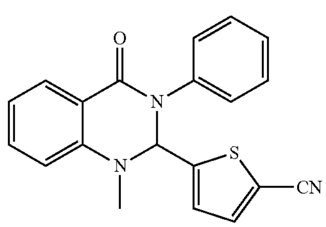 [SMILES: CN1c2ccccc2C(=O)N(c2ccccc2)C1c1ccc(C#N)s1] | 5-(1-Methyl-4-oxo-3-phenyl-1,2,3,4-tetrahydroquinazolin-2-yl)thiophene-2-carbonitrile |
| RN-3-066 | 54 | 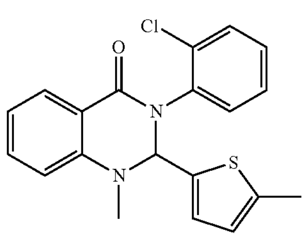 | 3-(2-chlorophenyl)-1-methyl-2-(5-methylthiophen-2-yl)-2,3-dihydroquinazolin-4(1H)-one |

-continued

| code | Compound | structure | name |
|---|---|---|---|
| RN-3-067 | 55 | 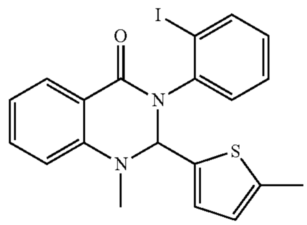 [SMILES: Cc1ccc(C2N(C)c3ccccc3C(=O)N2c2ccccc2I)s1] | 3-(2-iodophenyl)-1-methyl-2-(5-methylthiophen-2-yl)-2,3-dihydroquinazolin-4(1H)-one |
| RN-3-068 | 56 | 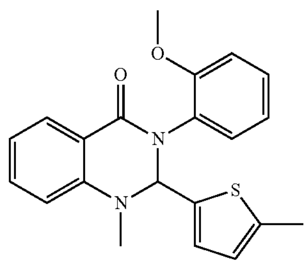 [SMILES: COc1ccccc1N1C(=O)c2ccccc2N(C)C1c1ccc(C)s1] | 3-(2-methoxyphenyl)-1-methyl-2-(5-methylthiophen-2-yl)-2,3-dihydroquinazolin-4(1H)-one |
| RN-3-069 | 57 | 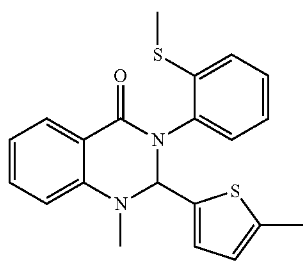 | 1-methyl-3-(2-(methylthio)phenyl)-2-(5-methylthiophen-2-yl)-2,3-dihydroquinazolin-4(1H)-one |
| RN-3-070 | 58 | 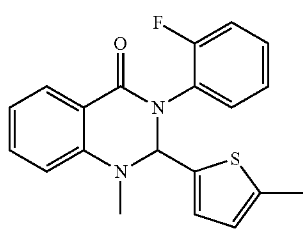 | 3-(2-fluorophenyl)-1-methyl-2-(5-methylthiophen-2-yl)-2,3-dihydroquinazolin-4(1H)-one |
| RN-3-089 | 59 | 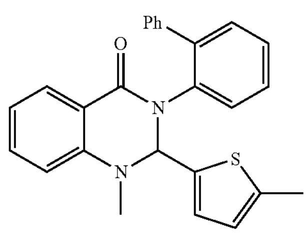 [SMILES: Cc1ccc(C2N(C)c3ccccc3C(=O)N2c2ccccc2-c2ccccc2)s1] | 3-([1,1'-biphenyl]-2-yl)-1-methyl-2-(5-methylthiophen-2-yl)-2,3-dihydroquinazolin-4(1H)-one |
| RN-3-098 | 60 | 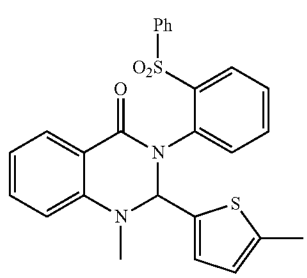 [SMILES: Cc1ccc(C2N(C)c3ccccc3C(=O)N2c2ccccc2S(=O)(=O)c2ccccc2)s1] | 1-methyl-2-(5-methylthiophen-2-yl)-3-(2-(phenylsulfonyl)phenyl)-2,3-dihydroquinazolin-4(1H)-one |

-continued

| code | Compound | structure | name |
|---|---|---|---|
| RN-3-122 | 61 | 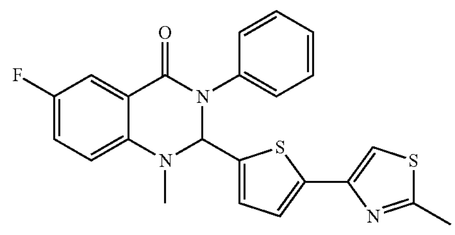 [SMILES: Cc1nc(-c2ccc(C3N(C)c4ccc(F)cc4C(=O)N3c3ccccc3)s2)cs1] | 6-fluoro-1-methyl-2-(5-(2-methylthiazol-4-yl)thiophen-2-yl)-3-phenyl-2,3-dihydroquinazolin-4(1H)-one |
| RN-3-061 | 62 | 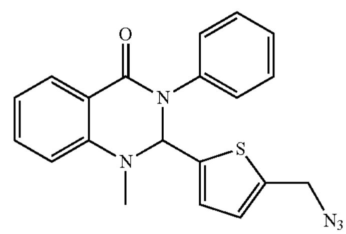 [SMILES: CN1c2ccccc2C(=O)N(c2ccccc2)C1c1ccc(CN=[N+]=[N-])s1] | 2-(5-(azidomethyl)thiophen-2-yl)-1-methyl-3-phenyl-2,3-dihydroquinazolin-4(1H)-one |
| VP37 | 63 | 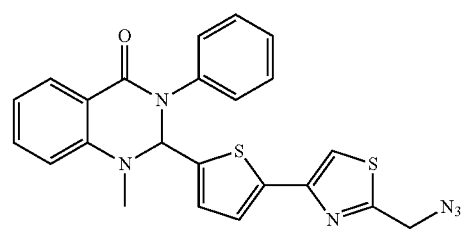 [SMILES: CN1c2ccccc2C(=O)N(c2ccccc2)C1c1ccc(-c2csc(CN=[N+]=[N-])n2)s1] | 2-(5-(2-(azidomethyl)thiazol-4-yl)thiophen-2-yl)-1-methyl-3-phenyl-2,3-dihydroquinazolin-4(1H)-one |
| VP153 | 64 | 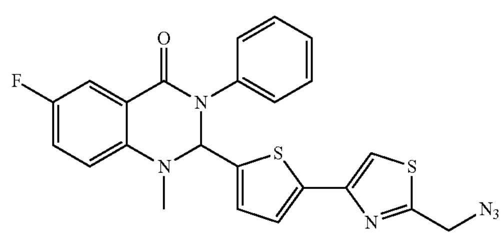 [SMILES: CN1c2ccc(F)cc2C(=O)N(c2ccccc2)C1c1ccc(-c2csc(CN=[N+]=[N-])n2)s1] | 2-(5-(2-(azidomethyl)thiazol-4-yl)thiophen-2-yl)-6-fluoro-1-methyl-3-phenyl-2,3-dihydroquinazolin-4(1H)-one |
| VP22 | 65 | 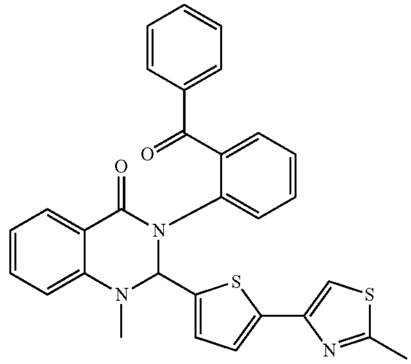 [SMILES: Cc1nc(-c2ccc(C3N(C)c4ccccc4C(=O)N3c3ccccc3C(=O)c3ccccc3)s2)cs1] | 3-(2-benzoylphenyl)-1-methyl-2-(5-(2-methylthiazol-4-ypthiophen-2-yl)-2,3-dihydroquinazolin-4(1H)-one |

-continued

| code | Compound | structure | name |
|---|---|---|---|
| VP104 | 66 | 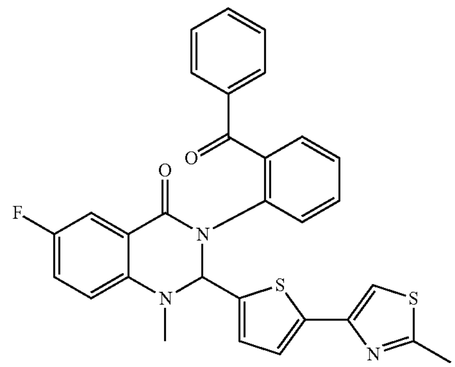 [SMILES: Cc1nc(-c2ccc(C3N(C)c4ccc(F)cc4C(=O)N3c3ccccc3C(=O)c3ccccc3)s2)cs1] | 3-(2-benzoylphenyl)-6-fluoro-1-methyl-2-(5-(2-methylthiazol-4-yl)thiophen-2-yl)-2,3-dihydroquinazolin-4(1H)-one |
| KH071-4 | 67 | 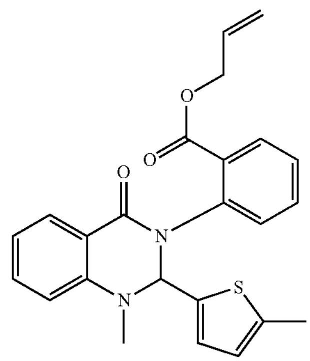 [SMILES: C=CCOC(=O)c1ccccc1N1C(=O)c2ccccc2N(C)C1c1ccc(C)s1] | allyl 2-(1-methyl-2-(5-methylthiophen-2-yl)-4-oxo-1,4-dihydroquinazolin-3(2H)-yl)benzoate |
| KH093-4 | 68 | 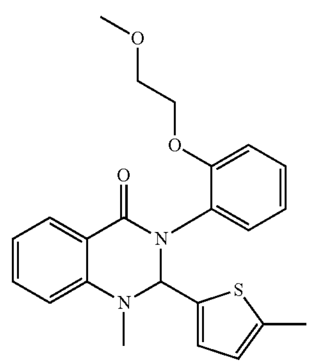 [SMILES: COCCOc1ccccc1N1C(=O)c2ccccc2N(C)C1c1ccc(C)s1] | 3-(2-(2-methoxyethoxy)phenyl)-1-methyl-2-(5-methylthiophen-2-yl)-2,3-dihydroquinazolin-4(1H)-one |
| KH112-2 | 69 | 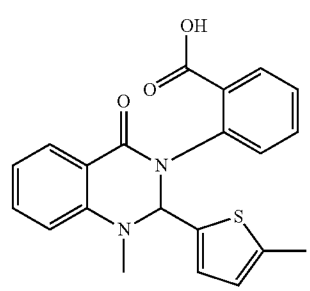 [SMILES: Cc1ccc(C2N(C)c3ccccc3C(=O)N2c2ccccc2C(=O)O)s1] | 2-(1-methyl-2-(5-methylthiophen-2-yl)-4-oxo-1,4-dihydroquinazolin-3(2H)-yl)benzoic acid |

In a particular embodiment of the invention, compounds of formula (I) are defined as follows:

$R^1$ is as previously defined: a hydrogen atom, a halogen atom or a $C_1$-$C_3$ alkoxy group; $R^1$ is preferably a hydrogen atom or a halogen atom and/or $R^1$ is substituted on the carbone C7 of the quinazolinone cycle;

$R^2$ is a phenyl radical optionally substituted by: a phenyl radical; a group —$CF_3$; a halogen atom, a group —$SO_2$-phenyl; a group —S—X or —O—X, X being a $C_1$-$C_4$ alkyl, preferably a methyl; a $C_1$-$C_4$ alkoxy group; a PEG substituent of general formula —($CH_2$—$CH_2$—O)$_n$—R with n=1 à 10, preferably n=1, and R is a hydrogen atom or a methyl group, preferably R is a methyl group; or a group —CO—O—Y or —CO—Y, Y being an hydrogen atom, a $C_1$-$C_4$ alkyl group, a phenyl radical or an allyl group (—$CH_2$—CH=$CH_2$);

$R^3$ is a thiophene cycle substituted on the C5' carbon of said thiophene cycle, the quinazolinone cycle being linked to the C2' carbon of said thiophene cycle, by:
a $C_1$-$C_3$ alkyl group, preferably a methyl;
a halogen atom;
a phenyl group optionally substituted by one or more of: $C_1$-$C_3$ alkoxy group, a group —CN, —$NO_2$, —COX or —COOX, X being a $C_1$-$C_4$ alkyl radical, preferably a methyl;
a group —SY, Y being a $C_1$-$C_4$ alkyl group or a phenyl group;
—CN;
a group —$CH_2$—$N_3$;
an aromatic heterocyclic group having 5 or 6 atoms, said aromatic heterocyclic group may be selected in the group consisting of furan, thiophene, pyrrole, pyrroline, pyrrolidine, dioxolane, oxazole, thiazole, imidazole, imidazoline, imidazolidine, pyrazole, isoxazole, isothiazole, pyran, pyridine, piperidine, dioxan, morpholine, pyridazine, pyrimidine, pyrazine, preferably, said aromatic heterocyclic group is a thiophene, pyridine, furan or thiazole; optionally substituted by at least one $C_1$-$C_3$ alkyl radical and/or a group —$CH_2$—$N_3$;
$R^4$ is a hydrogen atom or a methyl group;
with the proviso that compound of formula (I) is not such as $R^1$ is a hydrogen atom, $R^2$ is a phenyl group, $R^3$ is a 5-methylthiophen-2-yl group and $R^4$ is a hydrogen atom, or their pharmaceutically acceptable salts.

The chemical structure below shows the carbon atoms numbers used for defining the substituent positions in the compounds of this preferred embodiment of the invention:

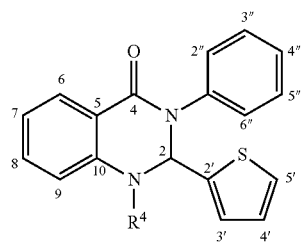

Preferably, $R^2$ is a phenyl cycle substituted on carbon C2" and/or $R^4$ is a methyl group.

In another particular embodiment of the invention, compounds of formula (I) are defined as follows:
$R^1$ is a hydrogen or a fluorine atom;
$R^2$ is a phenyl group, optionally substituted by a chlorine, iodine or fluorine atom, a —$OCH_3$, —$SCH_3$, —$SO_2$-phenyl or phenyl group;
$R^3$ is a thiophene group substituted by a methyl, ethyl, phenyl, —$SCH_3$, 2-thiophene, 2-furan, 3-furan, 2-pyridine, 4-(2-Me thiazole), S-phenyl group or a bromine atom, and
$R^4$ is a hydrogen atom or a methyl group;
with the proviso that compound of formula (I) is not such as $R^1$ is a hydrogen atom, $R^2$ is a phenyl group, $R^3$ is a 5-methylthiophen-2-yl group and $R^4$ is a hydrogen atom, or their pharmaceutically acceptable salts.

Preferred compounds of formula (I) are selected in the group consisting of compounds 7, 9, 13, 17, 18, 19, 20, 21, 25, 31, 32, 34, 35, 36, 37, 38, 39, 40, 41, 42, 43, 44, 47, 54, 55, 56, 57, 58, 59, 60 and 61.

Most preferred compounds of formula (I) are selected in the group consisting of compounds 7, 13, 17, 18, 19 and 20.

The compounds of formula (I) with $R^4$ being a hydrogen atom may be obtained from the Retro-2 analogs (see EP 2 145 873) by cyclization in basic medium (Pathway A) or by direct reaction between anthranilamide and aldehyde (pathway B):

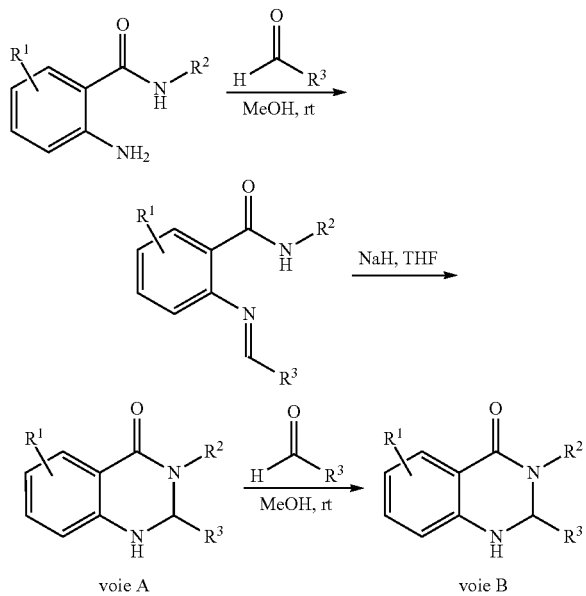

Compounds of formula (I) with $R^4$ being a methyl radical as represented hereafter:

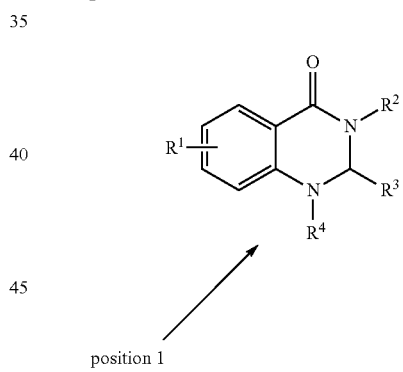

are obtained by deprotonation of the amine in position 1 and trapping of the anion with methyl iodure.

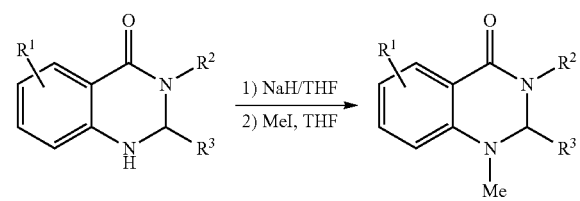

R1, R2 and R3 are as defined above.

Some of compounds according to the present invention (i.e. compounds 45, 46, 47, 48, 49, 50, 51 and 52) are prepared as follows:

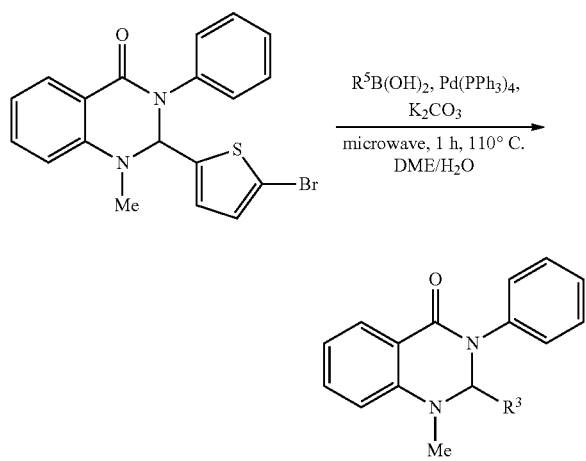

or by coupling compound 43 with PhSH catalyzed by $Pd_2dba_3$ (0.1 equiv.), dppf (0.15 equiv.) and tBuOK (2 equiv.) in dioxan, 1 hour at 140° C. in microwave (compound 44) or with $ZnCN_2$ catalyzed by $Pd_2dba_3$ (0.05 equiv.), dppf (0.1 equiv.) in DMF, 1 hour at 150° C. in microwave (compound 53).

Viruses entering cell by endocytosis include:

- filovirus such as members of the Ebolavirus family including Bundibugyo, Reston, Sudan, Tai Forest and Zaire; and Marburg virus;
- adenoviruses such as Adenovirus associated virus 2;
- arenavirus family including lymphocytic choriomeningitis virus;
- influenza A virus.

Viruses that are preferably treated by compounds of formula (I) are filoviruses, in particular Ebolaviruses.

The skilled person will adapt the formulation of compounds of formula (I) according to their physicochemical properties and their route of administration.

Said compounds of formula (I) can be administered orally (including buccal cavity or sublingually), parenterally, ocularly, nasally. Other possible interesting formulations include formulations for intraperitoneal (i.p), intravenous (i.v.), subcutaneous (s.c.), intramuscular (i.m.), transcutaneous, transdermal, intracathecal, epidural, submucosal adminstrations, pulmonary inhalation . . . . Compounds of formula (I) are preferably administered nasally, through the lung, orally or parenterally.

According to another aspect, the present invention pertains to a composition, especially a pharmaceutical composition, comprising at least one compound of formula (I). In addition to said compound of formula (I), the composition can comprise any pharmaceutical vehicle, stabilizer, adjuvant and the like as frequently used in the art.

The amount of compound of formula (I) administered to the mammal depends on activity of said compound, which may be measured in ways that are described in the examples. This quantity also depends on the severity of the pathology to treat; it finally depends on the age and weight of the individual to be treated.

In addition to the above provisions, the invention also comprises other provisions which will become clear from the description which follows, which refers to examples illustrating the biological activity of compounds of formula (I), and also to the attached drawings in which FIG. 1 represents inhibition of infection curves for tested compounds of the invention as described in the assays hereafter.

EXAMPLES

I. Synthesis of Compounds According to the Invention

General Procedure for the Synthesis of Compounds with $R^4$=H

To a solution of 2-aminobenzamides (4.71 mmol) in tetrahydrofuran (23 mL, 0.2M) was added the aldehyde (4.71 mmol) and p-toluene sulfonic acid (10 mol %, 0.5 mmol) in a sealed tube. The solution was warmed to 75° C. and stirred until complete consumption of starting materials (monitored by thin layer chromatography, usually overnight). After cooling to room temperature, silica was added and THF was evaporated. Purification by silica gel chromatography of the crude mixture yielded the expected compounds as solids.

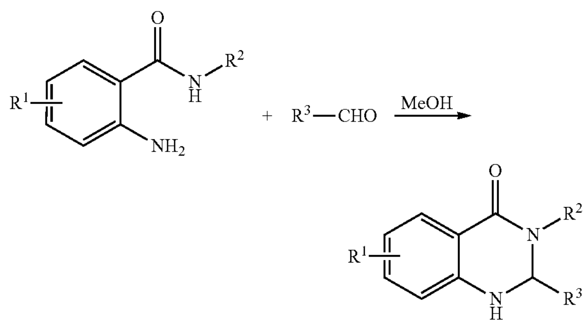

General Procedure for the Synthesis of Compounds with $R^4$=Me

To a mixture of NaH (1.5 equiv.) in anhydrous THF (0.3M) was added dropwise a solution of N—H tetrahydroquinazolin-4-one derivatives (1 equiv.) in anhydrous THF (0.5M) at 0° C. After 30 min, iodomethane (1.1 equiv.) was added dropwise. After 10 min, the solution was warmed to room temperature and stirred for 3 h. The reaction was then quenched with a saturated solution of $NaHCO_3$. The aqueous layer was then repeatedly extracted with $CH_2Cl_2$. The combined organic layers were then washed with a 1M solution of HCl (2×10 mL), dried over anhydrous $Na_2SO_4$, filtered and concentrated in vacuum. The purification by silica gel chromatography of the crude mixture yielded the expected compounds as solids.

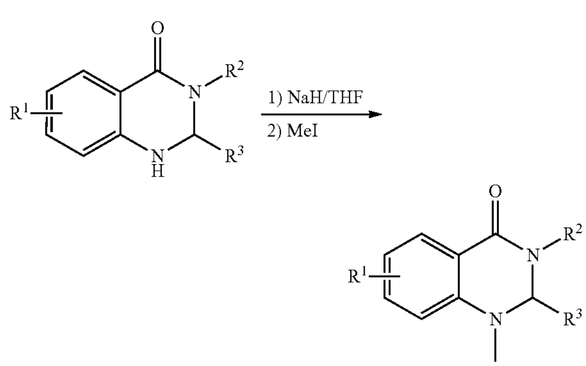

The different cyclic molecules, yields and purities obtained are listed in the Table I below:

TABLE I 2,3-dihydroquinazolin-4(1H)-one cyclic compounds ($R^4$ = H)

| code | compound | Name | yield | LC/MS | $^1$H | $^{13}$C |
|---|---|---|---|---|---|---|
| RN-1-013 | 1 | 2-(3-Methoxyphenyl)-3-phenyl-2,3-dihydroquinazolin-4(1H)-one | 88% | x | x | x |
| RN-1-019 | 2 | 2-(4-(Dimethylamino)phenyl)-3-phenyl-2,3-dihydroquinazolin-4(1H)-one | 77% | x | x | x |
| RN-1-021 | 3 | 2,3-Diphenyl-2,3-dihydroquinazolin-4(1H)-one | 84% | x | x | x |
| RN-1-027 | 4 | 2-(4-Methoxyphenyl)-3-phenyl-2,3-dihydroquinazolin-4(1H)-one | 78% | x | x | x |
| RN-1-066 | 5 | 2-(3-Methylthiophen-2-yl)-3-phenyl-2,3-dihydroquinazolin-4(1H)-one | 85% | x | x | x |
| RN-1-067 | 6 | 2-(4-Methylthiophen-2-yl)-3-phenyl-2,3-dihydroquinazolin-4(1H)-one | 65% | x | x | x |
| RN-1-068 | 7 | 2-(5-Ethylthiophen-2-yl)-3-phenyl-2,3-dihydroquinazolin-4(1H)-one | 77% | x | x | x |
| RN-1-086 | 8 | 3-((5R,7S)-3-Hydroxyadamantan-1-yl)-2-(5-methylthiophen-2-yl)-2,3-dihydroquinazolin-4(1H)-one | 81% | x | x | x |
| RN-1-100 | 9 | 2-(5-Bromothiophen-2-yl)-3-phenyl-2,3-dihydroquinazolin-4(1H)-one | 91% | x | x | x |
| RN-1-118 | 10 | 2-(5-Methylthiophen-2-yl)-3-(pyridin-3-yl)-2,3-dihydroquinazolin-4(1H)-one | 34% | x | x | x |
| RN-1-120 | 11 | 2-(5-Methylthiophen-2-yl)-3-(pyridin-4-yl)-2,3-dihydroquinazolin-4(1H)-one | 64% | x | x | x |
| RN-1-132 | 12 | 2-(5-Methylthiophen-2-yl)-3-(pyrimidin-4-yl)-2,3-dihydroquinazolin-4(1H)-one | 53% | x | x | x |
| RN-1-148 | 13 | 3-Phenyl-2-(5-phenylthiophen-2-yl)-2,3-dihydroquinazolin-4(1H)-one | 86% | x | x | x |
| RN-1-149 | 14 | 3-([1,1'-Biphenyl]-4-yl)-2-(5-methylthiophen-2-yl)-2,3-dihydroquinazolin-4(1H)-one | 73% | x | x | x |
| RN-1-151 | 15 | 2-(5-Methylthiophen-2-yl)-3-(3-(trifluoromethyl)phenyl)-2,3-dihydroquinazolin-4(1H)-one | 68% | x | x | x |
| RN-1-162 | 16 | 8-Methyl-2-(5-methylthiophen-2-yl)-3-phenyl-2,3-dihydroquinazolin-4(1H)-one | 99% | x | x | x |
| RN-1-173 | 17 | 2-(5-(Methylthio)thiophen-2-yl)-3-phenyl-2,3-dihydroquinazolin-4(1H)-one | 82% | x | x | — |
| RN-1-174 | 18 | 2-([2,2'-Bithiophen]-5-yl)-3-phenyl-2,3-dihydroquinazolin-4(1H)-one | 86% | x | x | x |
| RN-1-175 | 19 | 3-Phenyl-2-(5-(pyridin-2-yl)thiophen-2-yl)-2,3-dihydroquinazolin-4(1H)-one | 72% | x | x | x |
| RN-1-176 | 20 | 2-(5-(Furan-2-yl)thiophen-2-yl)-3-phenyl-2,3-dihydroquinazolin-4(1H)-one | 64% | x | x | x |
| RN-1-177 | 21 | 2-(5-(2-Methylthiazol-4-yl)thiophen-2-yl)-3-phenyl-2,3-dihydroquinazolin-4(1H)-one | 68% | x | x | x |
| RN-2-120 | 22 | 3-(4-Fluorophenyl)-2-(5-methylthiophen-2-yl)-2,3-dihydroquinazolin-4(1H)-one | 80% | x | x | x |
| RN-2-137 | 23 | 3-(2-Fluorophenyl)-2-(5-methylthiophen-2-yl)-2,3-dihydroquinazolin-4(1H)-one | 93% | x | x | x |
| RN-2-161 | 24 | 6-Methoxy-2-(5-methylthiophen-2-yl)-3-phenyl-2,3-dihydroquinazolin-4(1H)-one | 89% | x | x | x |
| RN-2-162 | 25 | 6-Fluoro-2-(5-methylthiophen-2-yl)-3-phenyl-2,3-dihydroquinazolin-4(1H)-one | 70% | x | x | x |
| RN-2-163 | 26 | 7-Fluoro-2-(5-methylthiophen-2-yl)-3-phenyl-2,3-dihydroquinazolin-4(1H)-one | 80% | x | x | x |

TABLE I-continued 2,3-dihydroquinazolin-4(1H)-one cyclic compounds (R⁴ = H)

| code | compound | Name | yield | LC/MS | $^1$H | $^{13}$C |
|---|---|---|---|---|---|---|
| RN-2-177 | 27 | 3-(4-Bromophenyl)-2-(5-methylthiophen-2-yl)-2,3-dihydroquinazolin-4(1H)-one | 80% | x | x | x |
| RN-2-178 | 28 | 3-(3-Bromophenyl)-2-(5-methylthiophen-2-yl)-2,3-dihydroquinazolin-4(1H)-one | 91% | x | x | x |
| RN-2-180 | 29 | 3-(4-Chlorophenyl)-2-(5-methylthiophen-2-yl)-2,3-dihydroquinazolin-4(1H)-one | 89% | x | x | x |
| RN-2-181 | 30 | 3-(3-Chlorophenyl)-2-(5-methylthiophen-2-yl)-2,3-dihydroquinazolin-4(1H)-one | 91% | x | x | x |
| RN-2-183 | 31 | 3-(2-(Methylthio)phenyl)-2-(5-methylthiophen-2-yl)-2,3-dihydroquinazolin-4(1H)-one | 79% | x | x | x |
| RN-2-182 | 32 | 3-(2-Chlorophenyl)-2-(5-methylthiophen-2-yl)-2,3-dihydroquinazolin-4(1H)-one | 92% | x | x | x |
| RN-2-199 | 33 | 6-Iodo-2-(5-methylthiophen-2-yl)-3-phenyl-2,3-dihydroquinazolin-4(1H)-one | 92% | | x | |
| RN-3-121 | 34 | 6-fluoro-2-(5-(2-methylthiazol-4-yl)thiophen-2-yl)-3-phenyl-2,3-dihydroquinazolin-4(1H)-one | 36% | x | x | x |

TABLE II 2,3-dihydroquinazolin-4(1H)-one compounds (R⁴ = methyl).

| code | compound | name | yield | LC/MS | $^1$H | $^{13}$C |
|---|---|---|---|---|---|---|
| RN-1-181 | 35 | 1-Methyl-2-(5-methylthiophen-2-yl)-3-phenyl-2,3-dihydroquinazolin-4(1H)-one | 85% à partir de RN-1-001 | x | x | x |
| RN-1-186 | 36 | 1-Methyl-3-phenyl-2-(5-phenylthiophen-2-yl)-2,3-dihydroquinazolin-4(1H)-one | 69% à partir de RN-1-069 | x | x | x |
| RN-1-192 | 37 | 1-Methyl-3-phenyl-2-(5-(pyridin-2-yl)thiophen-2-yl)-2,3-dihydroquinazolin-4(1H)-one | 97% à partir de RN-1-101 | x | x | x |
| RN-1-196 | 38 | 1-Methyl-2-(5-(methylthio)thiophen-2-yl)-3-phenyl-2,3-dihydroquinazolin-4(1H)-one | 91% à partir de RN-1-077 | x | x | x |
| RN-1-197 | 39 | 2-([2,2'-Bithiophen]-5-yl)-1-methyl-3-phenyl-2,3-dihydroquinazolin-4(1H)-one | 95% à partir de RN-1-080 | x | x | x |
| RN-2-001 | 40 | 2-(5-(Furan-2-yl)thiophen-2-yl)-1-methyl-3-phenyl-2,3-dihydroquinazolin-4(1H)-one | 97% à partir de RN-1-104 | x | x | x |
| RN-2-005 | 41 | 2-(5-Ethylthiophen-2-yl)-1-methyl-3-phenyl-2,3-dihydroquinazolin-4(1H)-one | 84% à partir de RN-1-068 | x | x | x |
| RN-2-015 | 42 | 1-Methyl-2-(5-(2-methylthiazol-4-yl)thiophen-2-yl)-3-phenyl-2,3-dihydroquinazolin-4(1H)-one | 83% à partir de RN-1-105 | x | x | x |
| RN-2-016 | 43 | 2-(5-Bromothiophen-2-yl)-1-methyl-3-phenyl-2,3-dihydroquinazolin-4(1H)-one | 85% à partir de RN-1-100 | x | x | x |
| RN-2-019 | 44 | 1-Methyl-3-phenyl-2-(5-(phenylthio)thiophen-2-yl)-2,3-dihydroquinazolin-4(1H)-one | 91% à partir de RN-2-016 | x | x | x |
| RN-2-029 | 45 | 2-(5-(3,4-Dimethoxyphenyl)thiophen-2-yl)-1-methyl-3-phenyl-2,3-dihydroquinazolin-4(1H)-one | 88% à partir de RN-2-016 | x | x | x |
| RN-2-032 | 46 | 1-Methyl-2-(5-(3-nitrophenyl)thiophen-2-yl)-3-phenyl-2,3-dihydroquinazolin-4(1H)-one | 90% à partir de RN-2-016 | x | x | x |

TABLE II-continued 2,3-dihydroquinazolin-4(1H)-one compounds ($R^4$ = methyl).

| code | compound | name | yield | LC/MS | $^1$H | $^{13}$C |
|---|---|---|---|---|---|---|
| RN-2-034 | 47 | 2-(5-(Furan-3-yl)thiophen-2-yl)-1-methyl-3-phenyl-2,3-dihydroquinazolin-4(1H)-one | 80% à partir de RN-2-016 | x | x | x |
| RN-2-049 | 48 | Methyl 4-(5-(1-methyl-4-oxo-3-phenyl-1,2,3,4-tetrahydroquinazolin-2-yl)thiophen-2-yl)benzoate | 80% à partir de RN-2-016 | x | x | x |
| RN-2-050 | 49 | 2-(5-(4-Acetylphenyl)thiophen-2-yl)-1-methyl-3-phenyl-2,3-dihydroquinazolin-4(1H)-one | 89% à partir de RN-2-016 | x | x | x |
| RN-2-053 | 50 | 1-Methyl-3-phenyl-2-(5-(3,4,5-trimethoxyphenyl)thiophen-2-yl)-2,3-dihydroquinazolin-4(1H)-one | 73% à partir de RN-2-016 | x | x | x |
| RN-2-057 | 51 | 1-methyl-2-(5-(4-methyl-3-nitrophenyl)thiophen-2-yl)-3-phenyl-2,3-dihydroquinazolin-4(1H)-one | 76% à partir de RN-2-016 | x | x | x |
| RN-2-059 | 52 | 4-(5-(1-Methyl-4-oxo-3-phenyl-1,2,3,4-tetrahydroquinazolin-2-yl)thiophen-2-yl)benzonitrile | 78% à partir de RN-2-016 | x | x | x |
| RN-3-012 | 53 | 5-(1-Methyl-4-oxo-3-phenyl-1,2,3,4-tetrahydroquinazolin-2-yl)thiophene-2-carbonitrile | 68% à partir de RN-2-016 | x | | |
| RN-3-066 | 54 | 3-(2-chlorophenyl)-1-methyl-2-(5-methylthiophen-2-yl)-2,3-dihydroquinazolin-4(1H)-one | 67% | x | x | x |
| RN-3-067 | 55 | 3-(2-iodophenyl)-1-methyl-2-(5-methylthiophen-2-yl)-2,3-dihydroquinazolin-4(1H)-one | 46% | x | x | x |
| RN-3-068 | 56 | 3-(2-methoxyphenyl)-1-methyl-2-(5-methylthiophen-2-yl)-2,3-dihydroquinazolin-4(1H)-one | 28% | x | x | x |
| RN-3-069 | 57 | 1-methyl-3-(2-(methylthio)phenyl)-2-(5-methylthiophen-2-yl)-2,3-dihydroquinazolin-4(1H)-one | 73% | x | x | x |
| RN-3-070 | 58 | 3-(2-fluorophenyl)-1-methyl-2-(5-methylthiophen-2-yl)-2,3-dihydroquinazolin-4(1H)-one | 51% | x | x | x |
| RN-3-089 | 59 | 3-([1,1'-biphenyl]-2-yl)-1-methyl-2-(5-methylthiophen-2-yl)-2,3-dihydroquinazolin-4(1H)-one | 74% | x | x | x |
| RN-3-098 | 60 | 1-methyl-2-(5-methylthiophen-2-yl)-3-(2-(phenylsulfonyl)phenyl)-2,3-dihydroquinazolin-4(1H)-one | 65% | x | x | x |
| RN-3-122 | 61 | 6-fluoro-1-methyl-2-(5-(2-methylthiazol-4-yl)thiophen-2-yl)-3-phenyl-2,3-dihydroquinazolin-4(1H)-one | 71% | x | x | x |

II. Measurement of the Protective Activity of Compounds Against Ebola

Experimental Protocol

Hela cells were seeded at a density of 50% into 96-well plates in MEM medium supplemented with 10% fetal bovine serum and incubated at 37° C., 5% $CO_2$. The cells were allowed to recover overnight. Drugs were dissolved in DMSO to 20 mM each. The following day each drug was diluted 100-fold into MEM with serum, serially diluted and then added in equal volume to the cell medium in each well. The final concentration of each drug is indicated in the figures. After 1 hour preincubation virus was added to a multiplicity of infection of 0.1. The virus used was a recombinant Ebolavirus that encodes green fluorescent protein (Towner et al. 2005. Virology 332:20-7). This virus is replication competent and shows normal pathogenesis in animals but expresses GFP 24 hours after infection has taken place. For this reason, the experiment was halted at 24 hours after virus challenge which was sufficient time for a single round of virus infection and expression of the GFP infection marker. The cells were then fixed in 10% Protocol Formalin for 24 hours. Cell nuclei were stained with DAPI following standard methods. The infection was then analyzed by photographing each well using an epifluorescent microscope. Total and infected cells were counted by counting DAPI stained cells and green fluorescent cells respectively using Cell Profiler software. The fraction of infected cells was calculated by dividing the number of green fluorescent cells by the total number of cells.

Results

IC50 is defined as the concentration of each drug that results in 50% inhibition of infection. Inhibition of infection was calculated as shown below:

$$\text{fraction infection} = \left( \frac{\text{number of green fluorescent cells}}{\text{number of } DAPI \text{ stained cell nuclei}} \right)$$

$$\text{inhibition (\%)} = 100 \times \left( 1 - \frac{\text{fraction infection after drug treatment}}{\text{fraction infection without treatment}} \right)$$

Each drug was tested at least four times and combined data used in calculations. Three parameter dose response curves were fitted to data by non-linear regression and IC50 values determined using Graphpad Prism 5 software (Table 3). The equation used is below:

$$Y = \text{lower plateau} + (\text{upper} - \text{lower plateau}) \div (1 + 10^{(X - \log IC50)})$$

Table III presents the results (compound IC50 in micromolar concentrations): the most potent compounds present the lower $IC_{50}$.

TABLE III

Evaluation of biological activities of compounds according to the present invention.

| molecule | compound | IC$_{50}$ (µM) |
|---|---|---|
| control | Retro-2$^{cycl}$ | 42.5 |
| RN-1-068 | 7 | 11.0 |
| RN-1-148 | 13 | 4.2 |
| RN-1-173 | 17 | 7.4 |
| RN-1-174 | 18 | 4.7 |
| RN-1-175 | 19 | 5.6 |
| RN-1-176 | 20 | 5.4 |
| RN-1-177 | 21 | 2.3 |

The Figure represents inhibition of infection curves for quinazolinones represented in Table III. Hela cells were treated for 1 hour with the indicated concentrations of each compound. Each compound was initially dissolved in DMSO to 20 mM and then diluted to a starting concentration of 100 µM and then by serial 2-fold dilution. This gave the highest concentration of DMSO as 0.5% (v/v) and was included as control and data shows the highest final concentration present with each compound at right (0.5% v/v) with serial 2-fold dilutions to the left. Three parameter dose response curves were fitted to data by non-linear regression using Graphpad Prism software (La Jolla, Calif., USA). The x-axis shows the concentrations of each compound as a Log$_2$ scale. Two graphs are shown to simplify data presentation. The same DMSO data is shown for each. A single representative experiment is shown.

All tested compounds of general formula (I) show a better activity compared to Retro-2$^{cycl}$.

The invention claimed is:

1. A method of treating a viral infection in a subject where the virus is a filovirus or an adenovirus, the method comprising administering to the subject a therapeutically effective amount of a compound of formula (I):

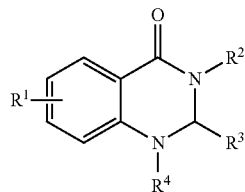

(I)

or a pharmaceutically acceptable salt thereof,
wherein:
$R^1$ is a hydrogen atom, a halogen atom or a $C_1$-$C_3$ alkoxy group;
$R^2$ is:
a phenyl radical,
a phenyl radical substituted by: a phenyl radical; a group —CF$_3$; a halogen atom; a group —SO$_2$-phenyl; a group —S—X or —O—X, X being a $C_1$-$C_4$ alkyl; a $C_1$-$C_4$ alkoxy group; a PEG substituent of general formula —(CH$_2$—CH$_2$—O)$_n$—R, in which n=1 to 10 and R is a hydrogen atom or a methyl group; or a group —CO—O—Y or —CO—Y, Y being an hydrogen atom, a $C_1$-$C_4$ alkyl group, a phenyl radical or an allyl group,
single or fused aromatic heterocyclic groups having 5 to 10 atoms and including one or two nitrogen atom(s),
an adamantyl group, or
an adamantyl group substituted by —OH;
$R^3$ is:
a thiophene group substituted by:
a phenyl group;
a phenyl group substituted by one or more of: a $C_1$-$C_3$ alkoxy group, and a group —CN, —NO$_2$, —COX and —COOX, X being a $C_1$-$C_4$ alkyl radical;
a group —SY, Y being a $C_1$-$C_4$ alkyl group or a phenyl group;
an aromatic heterocyclic group selected from the group consisting of furan, thiophene, pyrrole, pyrroline, pyrrolidine, dioxolane, oxazole, thiazole, imidazole, imidazoline, imidazolidine, pyrazole, isoxazole, isothiazole, pyran, pyridine, piperidine, dioxane, morpholine, pyridazine, pyrimidine and pyrazine, each of which is optionally substituted by at least one $C_1$-$C_3$ alkyl radical and/or a group —CH$_2$—N$_3$ thereof; and
$R^4$ is:
a hydrogen atom or a methyl group.

2. The method according to claim 1, wherein the compound of formula (I) is selected from the group consisting of:
3-phenyl-2-(5-phenylthiophen-2-yl)-2,3-dihydroquinazolin-4(1H)-one,
2-(5-(methylthio)thiophen-2-yl)-3-phenyl-2,3-dihydroquinazolin-4(1H)-one,
2-([2,2'-bithiophen]-5-yl)-3-phenyl-2,3-dihydroquinazolin-4(1H)-one,
3-phenyl-2-(5-(pyridin-2-yl)thiophen-2-yl)-2,3-dihydroquinazolin-4(1H)-one,
2-(5-(furan-2-yl)thiophen-2-yl)-3-phenyl-2,3-dihydroquinazolin-4(1H)-one,
2-(5-(2-methylthiazol-4-yl)thiophen-2-yl)-3-phenyl-2,3-dihydroquinazolin-4(1H)-one,
6-fluoro-2-(5-(2-methylthiazol-4-yl)thiophen-2-yl)-3-phenyl-2,3-dihydroquinazolin-4(1H)-one,
1-methyl-3-phenyl-2-(5-phenylthiophen-2-yl)-2,3-dihydroquinazolin-4(1H)-one,
1-methyl-3-phenyl-2-(5-(pyridin-2-yl)thiophen-2-yl)-2,3-dihydroquinazolin-4(1H)-one,
1-methyl-2-(5-(methylthio)thiophen-2-yl)-3-phenyl-2,3-dihydroquinazolin-4(1H)-one,
2-([2,2'-bithiophen]-5-yl)-1-methyl-3-phenyl-2,3-dihydroquinazolin-4(1H)-one,
2-(5-(furan-2-yl)thiophen-2-yl)-1-methyl-3-phenyl-2,3-dihydroquinazolin-4(1H)-one,
1-methyl-2-(5-(2-methylthiazol-4-yl)thiophen-2-yl)-3-phenyl-2,3-dihydroquinazolin-4(1H)-one,
1-methyl-3-phenyl-2-(5-(phenylthio)thiophen-2-yl)-2,3-dihydroquinazolin-4(1H)-one,
2-(5-(3,4-dimethoxyphenyl)thiophen-2-yl)-1-methyl-3-phenyl-2,3-dihydroquinazolin-4(1H)-one,
1-methyl-2-(5-(3-nitrophenyl)thiophen-2-yl)-3-phenyl-2,3-dihydroquinazolin-4(1H)-one, 2-(5-(furan-3-yl)thiophen-2-yl)-1-methyl-3-phenyl-2,3-dihydroquinazolin-4(1H)-one,
methyl 4-(5-(1-methyl-4-oxo-3-phenyl-1,2,3,4-tetrahydroquinazolin-2-yl)thiophen-2-yl)benzoate,
2-(5-(4-acetylphenyl)thiophen-2-yl)-1-methyl-3-phenyl-2,3-dihydroquinazolin-4(1H)-one,
1-methyl-3-phenyl-2-(5-(3,4,5-trimethoxyphenyl)thiophen-2-yl)-2,3-dihydroquinazolin-4(1H)-one,
1-methyl-2-(5-(4-methyl-3-nitrophenyl)thiophen-2-yl)-3-phenyl-2,3-dihydroquinazolin-4(1H)-one,
4-(5-(1-methyl-4-oxo-3-phenyl-1,2,3,4-tetra hydroquinazolin-2-yl)thiophen-2-yl)benzonitrile,
6-fluoro-1-methyl-2-(5-(2-methylthiazol-4-yl)thiophen-2-yl)-3-phenyl-2,3-dihydroquinazolin-4(1H)-one,
3-(2-benzoylphenyl)-1-methyl-2-(5-(2-methylthiazol-4-yl)thiophen-2-yl)-2,3-dihydroquinazolin-4(1H)-one,
3-(2-benzoylphenyl)-6-fluoro-1-methyl-2-(5-(2-methylthiazol-4-yl)thiophen-2-yl)-2,3-dihydroquinazolin-4(1H)-one, and
a pharmaceutically acceptable salt thereof.

3. The method according to claim 1 wherein:
$R^1$ is a hydrogen atom, a halogen atom or a $C_1$-$C_3$ alkoxy group;
$R^2$ is a phenyl radical, a phenyl radical substituted by: a phenyl radical; a group —$CF_3$; a halogen atom, a group —$SO_2$-phenyl; a group —S—X or —O—X, X being a $C_1$-$C_4$ alkyl; a $C_1$-$C_4$ alkoxy group; a PEG substituent of general formula —$(CH_2$—$CH_2$—$O)_n$—R, in which n=1 to 10, and R is a hydrogen atom or a methyl group; or a group —CO—O—Y or —CO—Y, Y being an hydrogen atom, a $C_1$-$C_4$ alkyl group, a phenyl radical or an allyl group;
$R^3$ is a thiophene substituted on the C5' carbon of the thiophene, the quinazolinone being linked to the C2' carbon of the thiophene by:
a phenyl group;
a phenyl group substituted by one or more of: a $C_1$-$C_3$ alkoxy group, a group —CN, —$NO_2$, —COX or —COOX, X being a $C_1$-$C_4$ alkyl radical;
a group —SY, Y being a $C_1$-$C_4$ alkyl group or a phenyl group; or
an aromatic heterocyclic group selected from the group consisting of furan, thiophene, pyrrole, pyrroline, pyrrolidine, dioxolane, oxazole, thiazole, imidazole, imidazoline, imidazolidine, pyrazole, isoxazole, isothiazole, pyran, pyridine, piperidine, dioxan, morpholine, pyridazine, pyrimidine, and pyrazine; and
$R^4$ is a hydrogen atom or a methyl group.

4. The method according to claim 1 wherein:
$R^1$ is a hydrogen or a fluorine atom;
$R^2$ is a phenyl group or a phenyl group substituted by a chlorine, iodine or fluorine atom, a —$OCH_3$, —$SCH_3$, —$SO_2$-phenyl or phenyl group;
$R^3$ is a thiophene group substituted by a phenyl, —$SCH_3$, 2-thiophene, 2-furan, 3-furan, 2-pyridine, 4-(2-Me thiazole) or a S-phenyl group, and
$R^4$ is a hydrogen atom or a methyl group.

5. The method according to claim 1, wherein $R^2$ is a phenyl radical substituted by the group —S—X or —O—X, X being a methyl.

6. The method according to claim 1, wherein $R^2$ is the phenyl radical substituted by a PEG substituent of general formula —$(CH_2$—$CH_2$—$O)_n$—R, in which n=1 and R is a hydrogen atom or a methyl group.

7. The method according to claim 1, wherein $R^2$ is a phenyl radical substituted by a PEG substituent of general formula —$(CH_2$—$CH_2$—$O)_n$—R, in which n=1 to 10 and R is a methyl group.

8. The method according to claim 1, wherein $R^2$ is pyridine.

9. The method according to claim 1, wherein $R^3$ is substituted by a phenyl group substituted by a group —CN, —$NO_2$, —COX or —COOX, X being a methyl.

10. The method according to claim 1, wherein the filovirus is Ebolavirus.

11. A method of treating a viral infection in a subject, comprising administering to the subject a therapeutically effective amount of A pharmaceutical composition comprising a compound of formula (I):

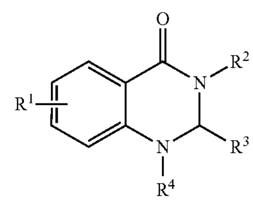

(I)

or a pharmaceutically acceptable salt thereof,
in combination with a pharmaceutically acceptable vehicle, wherein:
$R^1$ is a hydrogen atom, a halogen atom or a $C_1$-$C_3$ alkoxy group;
$R^2$ is:
a phenyl radical,
a phenyl radical substituted by: a phenyl radical; a group —$CF_3$; a halogen atom; a group —$SO_2$-phenYl; a group —S—X or —O—X, X being a $C_1$-$C_4$ alkyl; a $C_1$-$C_4$ alkoxy group; a PEG substituent of general formula —$(CH_2$—$CH_2$—$O)_n$—R, in which n=1 to 10 and R is a hydrogen atom or a methyl group; or a group —CO—O—Y or —CO—Y, Y being an hydrogen atom, a $C_1$-$C_4$ alkyl group, a phenyl radical or an allyl group,
single or fused aromatic heterocyclic groups having 5 to 10 atoms and including one or two nitrogen atom(s),
an adamantyl group, or
an adamantyl group substituted by —OH;
$R^3$ is:
a thiophene group substituted by:
a phenyl group:
a phenyl group substituted by one or more of: a $C_3$-$C_3$ alkoxy group, and a group —CN, —$NO_2$, —COX and —COOX, X being a $C_1$-$C_4$ alkyl radical;
a group —SY, Y being a $C_1$-$C_4$ alkyl group or a phenyl group;
an aromatic heterocyclic group selected from the group consisting of furan, thiophene, pyrrole, pyrroline, pyrrolidine, dioxolane, oxazole, thiazole, imidazole, imidazoline, imidazolidine, pyrazole, isoxazole, isothiazole, pyran, pyridine, piperidine, dioxane, morpholine, pyridazine, pyrimidine and pyrazine, each of which is optionally substituted by at least one $C_1$-$C_3$ alkyl radical and/or a group —$CH_2$—$N_3$ thereof; and R⁴ is:
  a hydrogen atom or a methyl group,
wherein the virus is selected from the group consisting of a filovirus and an adenovirus.

12. The method according to claim 11, wherein the filovirus is Ebolavirus.

13. The method according to claim 11, wherein the pharmaceutical composition is administered nasally, through the lung, orally or parenterally.

* * * * *